US006559154B2

(12) United States Patent
Kang et al.

(10) Patent No.: US 6,559,154 B2
(45) Date of Patent: May 6, 2003

(54) COMPOSITION OF SODIUM CHANNEL BLOCKING COMPOUND

(75) Inventors: Yuhong Kang, Nanning (CN); Frank Hay Kong Shum, North Vancouver (CA)

(73) Assignee: Nanning Maple Leaf Pharmaceutical Co., Ltd., Guangxi (CN)

( * ) Notice: Subject to any disclaimer, the term of this patent is extended or adjusted under 35 U.S.C. 154(b) by 0 days.

(21) Appl. No.: 09/819,796

(22) Filed: Mar. 29, 2001

(65) Prior Publication Data

US 2002/0119987 A1 Aug. 29, 2002

(30) Foreign Application Priority Data

Nov. 22, 2000 (CN) ........................................ 00132672 A

(51) Int. Cl.$^{7}$ ........................ A61K 31/505; A61K 31/44

(52) U.S. Cl. ........................................ 514/267; 514/282

(58) Field of Search ................................ 514/260, 257, 514/267, 282

(56) References Cited

U.S. PATENT DOCUMENTS

| | | | |
|---|---|---|---|
| 4,022,899 A | 5/1977 | Adams et al. | |
| 4,029,793 A | 6/1977 | Adams et al. | |
| 5,846,975 A * | 12/1998 | Pan et al. | 514/282 |
| 6,030,974 A * | 2/2000 | Schwartz et al. | 514/267 |

OTHER PUBLICATIONS

"Shaeroides oblongus: Cardiovascular and Respiratory Effects", Sanyal et al, Ind. J. Pharmc., 12 (2) 85–91, 1980.*

Bower et al., Clinical Toxicology, vol. 18, No. 7, pp. 813–863 (1981).

Kao, Pharmacological Reviews, vol. 18, No. 2, pp. 997–1049 (1966).

Kao et al., Pharmacology of Tarichatoxin, vol. 140, pp. 31–40 (1963).

Omana–Zapata et al., Pain, vol. 72, pp. 41–49 (1997).

Wallace, The Clinical Journal of Pain, vol. 16, No. 2, Supplement, pp. S80–85 (2000).

Yotsu et al., Agric. Biol. Chem., vol. 53, No. 3, pp. 893–895 (1989).

* cited by examiner

*Primary Examiner*—Zohreh Fay
*Assistant Examiner*—Brian-Yong Kwon
(74) *Attorney, Agent, or Firm*—Birch, Stewart, Kolasch & Birch, LLP

(57) ABSTRACT

The composition of the present invention comprises a sodium channel blocking compound which is capable of specifically binding to a site, either on an SS1 region or an SS2 region, on an extracellular region of a sodium channel alpha subunit, and a pharmaceutically acceptable carrier.

9 Claims, 27 Drawing Sheets

THE UV SPECTRUM OF TETRODOTOXIN INJECTION (990120-1A) IDENTIFICATION

TITLE:
SCAN SPEED: 120.0 nm/min
BANDPASS: 2.00nm

10: 0 AM /32/
RESPONSE: MEDIUM

| NO. | PEAK | | VALLEY | |
|---|---|---|---|---|
| 1 | 277.1 nm | 0.2364 Abs | 255.1 nm | 0.1247 Abs |
| 2 | 232.3 nm | 0.5380 Abs | | |

THE UV SPECTRUM OF TETRODOTOXIN INJECTION (990121-2A) IDENTIFICATION

TITLE:
SCAN SPEED: 120.0 nm/min
BANDPASS: 2.00nm

10: 0 AM /32/
RESPONSE: MEDIUM

| NO. | PEAK | | VALLEY | |
|-----|------|------|--------|------|
| 1 | 277.6 nm | 0.2357 Abs | 255.6 nm | 0.1243 Abs |
| 2 | 232.8 nm | 0.5365 Abs | | |

THE UV SPECTRUM OF TETRODOTOXIN INJECTION (990122-3A) IDENTIFICATION

10: 0 AM /32/
RESPONSE: MEDIUM

TITLE:
SCAN SPEED: 120.0 nm/min
BANDPASS: 2.00nm

| NO. | PEAK | | VALLEY | |
|---|---|---|---|---|
| 1 | 277.0 nm | 0.2355 Abs | 254.2 nm | 0.1240 Abs |
| 2 | 232.0 nm | 0.5364 Abs | | |

THE UV SPECTRUM OF TETRODOTOXIN CONTROL SAMPLE (S-1) IDENTIFICATION

TITLE:
SCAN SPEED: 120.0 nm/min
BANDPASS: 2.00nm

10: 0 AM /32/
RESPONSE: MEDIUM

| NO. | PEAK | | VALLEY | |
|---|---|---|---|---|
| 1 | 277.5 nm | 0.2174 Abs | 255.7 nm | 0.1120 Abs |
| 2 | 230.8 nm | 0.5393 Abs | | |

THE CHROMATOGRAM OF THE RETENTION TIME OF THE THREE BATCHES OF TETRODOTOXIN AND ITS CONTROL SAMPLE

THE HPLC CHROMATOGRAM OF CONTENT DETERMINATION
OF TETRODOTOXIN INJECTION (990120-1A)

CHANNEL A RESULTS

| PEAK | TIME | AREA | AREA % |
|---|---|---|---|
| 1 | 1.10 | 2044956 | 80.199 |
| 2 | 1.70 | 10066 | 0.395 |
| 3 | 18.02 | 383153 | 15.026 |
| 4 | 18.72 | 30817 | 1.209 |
| 5 | 19.37 | 80869 | 3.172 |
| TOTALS : | | 2549861 | 100.000 |

HPLC CHROMATOGRAM OF THE RECOVERY TEST OF TETRODOTOXIN INJECTION

D:\LHY\TTX\826030 - CHANNEL A

SOLUTION A: BLANK SOLUTION WITHOUT TETRODOTOXIN PREPARED AS THE FORMULA

CHANNEL A RESULTS

| PEAK | TIME | AREA | AREA % |
|---|---|---|---|

HPLC CHROMATOGRAM OF THE RECOVERY TEST OF TETRODOTOXIN INJECTION
D:\LHY\TTX\826018 - CHANNEL A

SOLUTION C: THE 0.2% ACETIC ACID SOLUTION CONTAINING THE PRIMARY PHARMACEUTICAL TETRODOTOXIN

CHANNEL A RESULTS

| PEAK | TIME | AREA | AREA % |
|---|---|---|---|
| 1 | 17.00 | 437132 | 64.590 |
| 2 | 19.35 | 29670 | 4.384 |
| 3 | 19.67 | 20746 | 3.065 |
| 4 | 20.27 | 39415 | 5.824 |
| 5 | 21.93 | 34289 | 5.066 |
| 6 | 23.82 | 30002 | 4.433 |
| 7 | 25.15 | 85526 | 12.637 |
| TOTALS : | | 676730 | 100.000 |

HPLC CHROMATOGRAM OF THE RECOVERY TEST OF TETRODOTOXIN INJECTION
D:\LHY\TTX\826019 - CHANNEL A

SOLUTION D; SOLUTION A CONTAINING THE PRIMARY PHARMACEUTICAL TETRODOTOXIN

CHANNEL A RESULTS

| PEAK | TIME | AREA | AREA % |
|---|---|---|---|
| 1 | 16.82 | 444093 | 62.900 |
| 2 | 19.17 | 42294 | 5.990 |
| 3 | 19.52 | 22777 | 3.226 |
| 4 | 20.15 | 39475 | 5.591 |
| 5 | 21.65 | 42344 | 6.139 |
| 6 | 23.53 | 30147 | 4.270 |
| 7 | 24.75 | 83898 | 11.883 |
| TOTALS : | | 706028 | 100.000 |

DAY 0 CHROMATOGRAM OF TTX INJECTION SAMPLES
(BATCH 990120-1A)

CHANNEL A RESULTS

| PEAK | TIME | AREA | AREA % |
|---|---|---|---|
| 1 | 16.60 | 457304 | 67.543 |
| 2 | 21.28 | 96642 | 14.274 |
| 3 | 24.32 | 123111 | 18.183 |
| TOTALS : | | 677057 | 100.000 |

DAY 5 CHROMATOGRAM OF TTX INJECTION SAMPLES
(BATCH 990120-1A) EXPOSED TO FLUORESCENCE LIGHT

CHANNEL A RESULTS

| PEAK | TIME | AREA | AREA % |
|---|---|---|---|
| 1 | 16.87 | 439230 | 64.337 |
| 2 | 19.20 | 33194 | 4.862 |
| 3 | 19.55 | 21996 | 3.222 |
| 4 | 20.18 | 41813 | 6.125 |
| 5 | 21.70 | 38117 | 5.583 |
| 6 | 23.58 | 26835 | 3.931 |
| 7 | 24.83 | 81513 | 11.940 |
| TOTALS : | | 682698 | 100.000 |

DAY 10 CHROMATOGRAM OF TTX INJECTION SAMPLES (BATCH 990120-1A) EXPOSED TO FLUORESCENCE LIGHT

CHANNEL A RESULTS

| PEAK | TIME | AREA | AREA % |
|---|---|---|---|
| 1 | 16.78 | 440996 | 64.617 |
| 2 | 19.13 | 40110 | 5.877 |
| 3 | 19.50 | 21413 | 3.138 |
| 4 | 20.12 | 38546 | 5.648 |
| 5 | 21.55 | 38558 | 5.650 |
| 6 | 23.45 | 25316 | 3.709 |
| 7 | 24.67 | 77538 | 11.361 |
| TOTALS : | | 682477 | 100.000 |

DAY 5 CHROMATOGRAM OF TTX INJECTION SAMPLES
(BATCH 990120-1A) STORED AT 40°C

CHANNEL A RESULTS

| PEAK | TIME | AREA | AREA % |
|---|---|---|---|
| 1 | 16.68 | 403338 | 62.647 |
| 2 | 19.07 | 31695 | 4.923 |
| 3 | 19.38 | 18661 | 2.898 |
| 4 | 20.00 | 26281 | 4.082 |
| 5 | 21.38 | 37923 | 5.890 |
| 6 | 23.28 | 16412 | 2.549 |
| 7 | 24.50 | 109512 | 17.010 |
| TOTALS : | | 643822 | 100.000 |

DAY 10 CHROMATOGRAM OF TTX INJECTION SAMPLES
(BATCH 990120-1A)

CHANNEL A RESULTS

| PEAK | TIME | AREA | AREA % |
|---|---|---|---|
| 1 | 16.68 | 406902 | 62.061 |
| 2 | 19.12 | 81196 | 4.757 |
| 3 | 19.45 | 16602 | 2.563 |
| 4 | 20.07 | 14841 | 2.264 |
| 5 | 20.38 | 10273 | 1.567 |
| 6 | 21.40 | 32718 | 4.990 |
| 7 | 23.30 | 14349 | 2.265 |
| 8 | 24.52 | 128073 | 19.534 |
| TOTALS : | | 655644 | 100.000 |

DAY 5 CHROMATOGRAM OF TTX INJECTION SAMPLES
(BATCH 990120-1A) STORED AT 60°C

CHANNEL A RESULTS

| PEAK | TIME | AREA | AREA % |
|---|---|---|---|
| 1 | 16.67 | 320463 | 43.726 |
| 2 | 19.10 | 55618 | 7.589 |
| 3 | 19.45 | 20052 | 2.736 |
| 4 | 20.07 | 13250 | 1.808 |
| 5 | 20.40 | 13195 | 1.800 |
| 6 | 21.38 | 62082 | 8.471 |
| 7 | 23.28 | 17525 | 2.391 |
| 8 | 24.50 | 230698 | 31.478 |
| TOTALS : | | 732883 | 100.000 |

DAY 10 CHROMATOGRAM OF TTX INJECTION SAMPLES (BATCH 990120-1A)STORED AT 60°C

CHANNEL A RESULTS

| PEAK | TIME | AREA | AREA % |
|---|---|---|---|
| 1 | 16.63 | 312079 | 43.881 |
| 2 | 19.05 | 49723 | 6.992 |
| 3 | 19.40 | 20080 | 2.823 |
| 4 | 20.05 | 15408 | 2.167 |
| 5 | 21.32 | 67030 | 9.425 |
| 6 | 23.23 | 21349 | 3.002 |
| 7 | 24.42 | 225521 | 31.710 |
| TOTALS : | | 711190 | 100.000 |

DAY 5 CHROMATOGRAM OF TTX INJECTION SAMPLES
(BATCH 990120-1A) STORED AT 80°C

D:\LHY\TTX\617033 - CHANNEL A

CHANNEL A RESULTS

| PEAK | TIME | AREA | AREA % |
|---|---|---|---|
| 1 | 16.88 | 225642 | 27.595 |
| 2 | 19.27 | 189762 | 23.207 |
| 3 | 20.82 | 29663 | 3.628 |
| 4 | 21.73 | 75156 | 9.191 |
| 5 | 23.58 | 37486 | 4.584 |
| 6 | 24.88 | 259987 | 31.795 |
| TOTALS : | | 817696 | 100.000 |

DAY 10 CHROMATOGRAM OF TTX INJECTION SAMPLES
(BATCH 990120-1A) STORED AT 80°C

D:\LHY\TTX\617078 - CHANNEL A

CHANNEL A RESULTS

| PEAK | TIME | AREA | AREA % |
|---|---|---|---|
| 1 | 16.65 | 201979 | 36.363 |
| 2 | 19.03 | 106755 | 19.220 |
| 3 | 20.05 | 9113 | 1.641 |
| 4 | 21.33 | 24854 | 4.475 |
| 5 | 23.22 | 5678 | 1.022 |
| 6 | 24.45 | 207069 | 37.280 |
| TOTALS : | | 555448 | 100.000 |

DAY 5 CHROMATOGRAM OF TTX INJECTION SAMPLES (BATCH 990120-1A) STORED AT THE HUMIDITY OF 75%

CHANNEL A RESULTS

| PEAK | TIME | AREA | AREA % |
|---|---|---|---|
| 1 | 17.03 | 440743 | 57.272 |
| 2 | 19.00 | 19869 | 2.582 |
| 3 | 19.22 | 16741 | 2.175 |
| 4 | 19.42 | 30163 | 3.920 |
| 5 | 20.10 | 65769 | 8.546 |
| 6 | 22.07 | 50126 | 6.514 |
| 7 | 23.82 | 52224 | 6.786 |
| 8 | 25.23 | 93927 | 12.205 |
| TOTALS : | | 769562 | 100.000 |

DAY 10 CHROMATOGRAM OF TTX INJECTION SAMPLES
(BATCH 990120-1A) STORED AT THE HUMIDITY OF 75%

CHANNEL A RESULTS

| PEAK | TIME | AREA | AREA % |
|---|---|---|---|
| 1 | 16.87 | 447357 | 58.043 |
| 2 | 19.17 | 25793 | 3.347 |
| 3 | 19.43 | 23024 | 2.987 |
| 4 | 19.95 | 20972 | 2.721 |
| 5 | 20.40 | 50791 | 6.590 |
| 6 | 21.22 | 21996 | 2.854 |
| 7 | 21.72 | 56974 | 7.392 |
| 8 | 23.60 | 31567 | 4.096 |
| 9 | 24.88 | 92256 | 11.970 |
| TOTALS : | | 770730 | 100.000 |

DAY 5 CHROMATOGRAM OF TTX INJECTION SAMPLES
(BATCH 990120-1A)STORED AT THE HUMIDITY OF 92.5%

CHANNEL A RESULTS

| PEAK | TIME | AREA | AREA % |
|---|---|---|---|
| 1 | 16.82 | 447441 | 61.629 |
| 2 | 19.17 | 34832 | 4.798 |
| 3 | 19.52 | 23418 | 3.226 |
| 4 | 20.15 | 41630 | 5.734 |
| 5 | 21.65 | 47836 | 6.589 |
| 6 | 23.53 | 35696 | 4.917 |
| 7 | 24.75 | 95165 | 13.108 |
| TOTALS : | | | |
| | | 726018 | 100.000 |

DAY 10 CHROMATOGRAM OF TTX INJECTION SAMPLES
(BATCH 990120-1A) STORED AT THE HUMIDITY OF 92.5%

CHANNEL A RESULTS

| PEAK | TIME | AREA | AREA % |
|---|---|---|---|
| 1 | 16.88 | 439985 | 62.732 |
| 2 | 19.17 | 24726 | 3.525 |
| 3 | 19.42 | 20133 | 2.871 |
| 4 | 19.93 | 18443 | 2.630 |
| 5 | 20.37 | 43002 | 6.131 |
| 6 | 21.17 | 18768 | 2.676 |
| 7 | 21.72 | 29564 | 4.215 |
| 8 | 23.65 | 14957 | 2.133 |
| 9 | 24.90 | 91798 | 13.088 |
| TOTALS : | | 701376 | 100.000 |

MONTH 1 CHROMATOGRAM OF TTX INJECTION SAMPLES
(BATCH 990120-1A) IN ACCELERATION TEST AT 40°C

CHANNEL A RESULTS

| PEAK | TIME | AREA | AREA % |
|---|---|---|---|
| 1 | 17.98 | 376984 | 44.357 |
| 2 | 19.38 | 21365 | 2.514 |
| 3 | 20.47 | 22100 | 2.600 |
| 4 | 21.63 | 46498 | 5.471 |
| 5 | 22.87 | 157085 | 18.483 |
| 6 | 24.47 | 12261 | 1.443 |
| 7 | 25.03 | 28093 | 3.306 |
| 8 | 26.18 | 185497 | 21.826 |
| TOTALS : | | 849883 | 100.000 |

MONTH 2 CHROMATOGRAM OF TTX INJECTION SAMPLES
(BATCH 990120-1A) IN ACCELERATION TEST AT 40°C

CHANNEL A RESULTS

| PEAK | TIME | AREA | AREA % |
|---|---|---|---|
| 1 | 16.55 | 342810 | 51.051 |
| 2 | 18.92 | 59383 | 8.843 |
| 3 | 19.65 | 15557 | 2.117 |
| 4 | 21.17 | 42516 | 6.331 |
| 5 | 24.28 | 211244 | 31.458 |
| TOTALS : | | 671510 | 100.000 |

D:\LHY\TTX\826029 - CHANNEL A

CHANNEL A RESULTS

| PEAK | TIME | AREA | AREA % |
|---|---|---|---|
| 1 | 16.48 | 343552 | 55.945 |
| 2 | 18.87 | 14545 | 2.369 |
| 3 | 19.48 | 12851 | 2.293 |
| 4 | 21.02 | 39941 | 6.504 |
| 5 | 24.08 | 203193 | 33.089 |
| TOTALS : | | 614082 | 100.000 |

MONTH 1 CHROMATOGRAM OF TTX INJECTION SAMPLES
(BATCH 990120-1A) STORED AT 4-5°C

CHANNEL A RESULTS

| PEAK | TIME | AREA | AREA % |
|---|---|---|---|
| 1 | 16.53 | 12642 | 1.366 |
| 2 | 17.92 | 469198 | 50.691 |
| 3 | 20.62 | 53889 | 5.822 |
| 4 | 21.15 | 78215 | 8.450 |
| 5 | 21.60 | 28495 | 3.075 |
| 6 | 21.93 | 27149 | 2.933 |
| 7 | 22.77 | 75205 | 8.125 |
| 8 | 23.37 | 32292 | 3.489 |
| 9 | 24.93 | 38038 | 4.110 |
| 10 | 26.10 | 110521 | 11.940 |
| TOTALS : | | 925608 | 100.000 |

MONTH 3 CHROMATOGRAM OF TTX INJECTION SAMPLES
(BATCH 990120-1A) STORED AT 4-5°C

D:\LHY\TTX\826032 - CHANNEL A

CHANNEL A RESULTS

| PEAK | TIME | AREA | AREA % |
|---|---|---|---|
| 1 | 16.87 | 446937 | 73.393 |
| 2 | 19.17 | 19824 | 3.255 |
| 3 | 19.43 | 15306 | 2.513 |
| 4 | 19.95 | 11884 | 1.952 |
| 5 | 20.40 | 18910 | 3.105 |
| 6 | 23.60 | 13018 | 2.138 |
| 7 | 24.88 | 83086 | 13.644 |
| TOTALS : | | 608965 | 100.000 |

D:\LHY\TTX\826033 - CHANNEL A

CHANNEL A RESULTS

| PEAK | TIME | AREA | AREA % |
|---|---|---|---|
| 1 | 16.77 | 447336 | 75.939 |
| 2 | 19.13 | 28063 | 4.764 |
| 3 | 19.52 | 10316 | 1.751 |
| 4 | 21.53 | 10525 | 1.787 |
| 5 | 23.47 | 15842 | 2.689 |
| 6 | 14.65 | 76989 | 13.070 |
| TOTALS : | | 589071 | 100.000 |

MONTH 6 CHROMATOGRAM OF TTX INJECTION SAMPLES (BATCH 990120-1A) STORED AT 4-5°C

CHANNEL A RESULTS

| PEAK | TIME | AREA | AREA % |
|---|---|---|---|
| 1 | 1.10 | 1329668 | 73.593 |
| 2 | 14.60 | 369604 | 20.456 |
| 3 | 15.43 | 67516 | 3.737 |
| 4 | 22.18 | 40001 | 2.214 |
| TOTALS : | | 1806789 | 100.000 |

COMPOSITION OF SODIUM CHANNEL BLOCKING COMPOUND

FIELD OF INVENTION

The present invention relates to pharmaceutical compositions comprising at least one sodium channel blocking compound in a suitable pharmaceutical vehicle.

BACKGROUND OF THE INVENTION

The methods and compositions of the present invention provide a solution that meets the requirements for clinical use. The formulation can be administered systemically for indications including, but not limited to, pain requiring analgesia and treatment of drug dependence (See, U.S. Pat. No. 5,846,975). The formulation can be administered as described in A Method of Analgesia, Dong Q. et al, U.S. patent application Ser. No. 09/695,053, filed Oct. 25, 2000, Attorney Docket No. 3519-0103P.

Tetrodotoxin is a nonprotein neurotoxin with potent activity. It is found in diverse animal species, including puffer fish, goby fish, newt, frogs and the blue-ringed octopus.

As sodium channel blocking compounds with high selectivity, tetrodotoxin and saxitoxin specifically bind to a site on an extracellular region, either an SS1 region or an SS2 region, of a sodium channel alpha subunit. Surprisingly, compounds binding the SS1 or SS2 region of a sodium channel can produce long-acting and potent analgesia or anesthesia with no severe adverse effects (Dong Q. et al, supra, and Ku B. et al, U.S. patent application Ser. No. 09/702,826, filed Nov. 1, 2000, Attorney Docket No. 3519-0106P).

Tetrodotoxin (TTX) has a chemical formula of $C_{11}H_{17}N_3O_8$, and has a molecular weight of 319.28. The Merck Index, $10^{th}$ Ed. (1983), states tetrodotoxin is the generic name for the compound octahydro-12-(hydroxymethyl)-2-imino-5,9:7,10a-dimethano-10aH-(1,3) dioxocino(6,5-d)-pyrimidine-4,7,10,11, 12-pentol, which has the following structure:

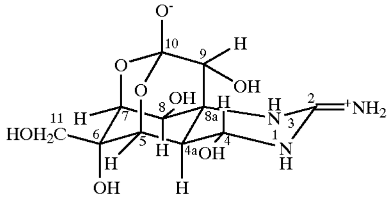

The TTX molecule consists of a perhydroquinozoline group with a guanidine and six hydroxyls. Pure TTX is a white crystalline powder, odorless and tasteless. It turns black around 220° C. without decomposition. TTX is soluble in acidic aqueous solution, but is not soluble in organic solvents. The pKa (aqueous) of TTX is 8.76. Thus TTX is a basic alkaloid. Aqueous solution of strong acids can decompose TTX, so usually TTX is dissolved in an aqueous solution of a weak organic acid. TTX is relatively thermally stable in neutral to weakly acidic solutions, but will be destroyed promptly in a strongly acidic or basic aqueous solution.

The present invention utilizes tetrodotoxin having a purity of at least 96% as the primary drug substance. Tetrodotoxin can be obtained by the technology described in A Method of Extracting Tetrodotoxin, Zhou M. et al, U.S. patent application Ser. No. 09/695,711, filed Oct. 25, 2000, Attorney Docket No. 3519-0101P. Further purification of TTX is described in Chinese patent application no.00132673.2, filed Nov. 22, 2000 and in U.S. patent application Ser. No. 09/818,863, filed Mar. 28, 2001, Attorney Docket No. 3519-0110P.

Analogs of tetrodotoxin can be used in the formulation of the invention. Preferred analogs of TTX are anhydrotetrodotoxin, tetrodaminotoxin, methoxytetrodotoxin, ethoxytetrodotoxin, deoxytetrodotoxin and tetrodonic acid.

Because TTX decomposes readily in gastric acid, oral ingestion is not considered to be a favored route of administration. Therefore, the compositions of the present invention are mainly for injection, preferably intramuscular injection. Most injectable formulations are solutions, and such properties as solubility, stability and safety of the drug must be considered when designing an injection (Bi D., Pharmaceutics, $4^{th}$ Edition).

The calculation of the dose of TTX for injection is based upon the results of pre-clinical pharmacology and pharmacodynamics studies. The calculation of the clinical pharmaceutical dosage is based upon the dosage effective in animals. In general, it is calculated as ⅕ of the effective animal dosage. 50, 60, and 70 kg are used as human body weights, respectively.

The TTX analgesic $ID_{50}$ (half inhibition dosage) in the acetic acid-induced twisting test in mice is 2.80 μg/kg (intramuscularly, IM). Accordingly, the recommended clinical dosage for humans is:

$$2.80\ \mu g/kg \times (1/5) \times 50\ (60,\ 70) kg = 28.0\ (33.6,\ 39.2) \mu g$$

The TTX effective dosage in the formalin-induced inflammation test in rats is 2.5 μg/mg (IM) (P<0.01). Accordingly, the recommended clinical dosage for humans is:

$$2.50\ \mu g/kg \times (1/5) \times 50\ (60,\ 70) kg = 25.0\ (30.0,\ 35.0) \mu g$$

It is also possible to calculate the initial clinical dosage based upon $LD_{50}$ value. Considering the results of pharmacodynamics studies, the clinical dosage can be calculated as 1/50 of the $LD_{50}$. 50, 60, and 70 kg are used as human body weights, respectively. Our most recent study shows that the $LD_{50}$ in mice is 11.1 μg/kg (im), therefore, the suggested clinical dose is:

$$11.1\ \mu g/kg \times 1/50 \times 50(60,70) kg = 11.1(13.32,15.54) \mu g$$

Based upon the results of pharmacology studies and knowledge in the art, the concentration of TTX for injection is designed to be 15 μg/mL, and the fill of a TTX injection is typically 1 or 2 mL.

TTX is a perhydroquinozoline compound that is only slightly soluble in water but soluble in an aqueous solution having an acidic or basic pH. Therefore, such commonly used auxiliary solvents as dilute acetic acid, hydrochloric acid and citric acid can be used dissolve TTX for formulation. Maintaining an acidic pH helps ensure the stability of a TTX formulation, as TTX is rather stable in weakly acidic solutions. The acid is preferably a weak organic acid, and formic acid, acetic acid or propionic acid is preferred.

It is preferable to include an adequate buffer, such as an acetate buffer, a citrate buffer, a phosphate buffer or a borate buffer, for the purpose of maintaining the pH of the formulation in an acceptable range. We have found (See Example 1) that the pH of a TTX formulation should be kept between 3.5–7.0, more preferably between 3.5–5.0. The buffer can be added in an amount of up to 0.5% by weight of the formulation. (A density of 1 g/ml is assumed for the formulated product.) As an example, a mixture of 55.5 ml of a 0.2M acetic acid solution and 4.5 ml of a 0.2M sodium acetate solution can be made, then added to a formulation in an amount of up to 5% by volume of the formulation. In this example, the buffer will constitute about 0.06% by weight of the formulation. Thus, the buffer can typically constitute about 0.1% by weight of the formulation.

In addition, a mixed solvent consisting of a glycol, preferably a $C_2$–$C_6$ alkane glycol, most preferably propylene glycol, and water is also desirable for improving the stability of TTX in a formulation. Addition of the glycol to the formulation results in acceptable stability with use of higher pH, providing a formulation that is more tolerated by the patient upon injection.

Environmental factors, such as temperature, light, humidity, and oxygen, were studied to determine their influence on the stability of TTX formulation so that a formulation and manufacturing technology that meet quality requirements can be devised. Test results (See Example 4) demonstrate that humidity and light have no significant effect on a TTX formulation, but increasing temperature will cause the content of TTX to decline. Therefore, a TTX formulation should be stored at low temperature so as to ensure its stability.

More components may be added to a TTX formulation in consideration of improving performance and convenience of storage, including viscosity increasing agents such as polyvinyl alcohol, celluloses, such as hydroxypropyl methyl cellulose and carbomer; preservatives, such as benzalkonium chloride, chlorobutanol, phenylmercuric acetate and phenyl mercuric nitrate; tonicity adjusters, such as sodium chloride, mannitol and glycerine; and penetration enhancers, such as glycols, oleic acid, alkyl amines and the like. A vasoconstrictor can also be added to the formulation. Combination formulations including the long-acting sodium channel blocking compound and an antibiotic, a steroidal or a non-steroidal anti-inflammatory drug and/or a vasoconstrictor are contemplated.

Regarding drug safety, examples described in A Method of Analgesia, Dong Q. et al, supra, have shown that TTX formulation complies with requirements for low toxicity, low hemolyzation and low local irritation. Dong Q. et al has also indicated that administration of a TTX formulation has no severe or non-reversible adverse effects.

A preferred composition of the present invention comprises substance of tetrodotoxin having a purity of 96% or higher as an active ingredient, an auxiliary solvent selected from dilute acetic acid, dilute hydrochloridic and citric acid, and a 5% acetic acid-sodium acetate buffer to maintain the pH between 3.5–5.0. High temperature should be avoided during manufacture of the formulation, and sterile processing is preferred. Excessive exposure to direct sunlight should be avoided during transportation, and it is recommended that the finished product be stored in a cool place, preferably at 4–20° C.

Saxitoxin has physical and chemical properties similar to tetrodotoxin. Saxitoxin is found in dinoflagellates, which include Alexandrium tamarense, Gymnodinium catenatum, and Pyrodinium bahamense. Saxitoxin has the following structure:

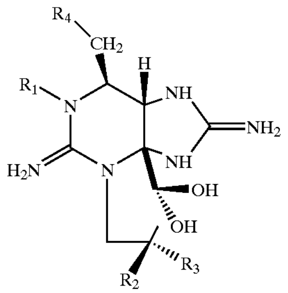

Saxitoxin is also stable in acidic solutions. Saxitoxin is a highly selective sodium channel blocker and produces analgesia or anesthesia by this mechanism. Therefore, saxitoxin can be used in the same manner as TTX in the compositions of the present invention.

The formulation of the present invention can optionally contain an auxiliary solvent selected from dilute acetic acid, dilute hydrochloric acid or citric acid, and a buffer selected from acetate buffers, citrate buffers, phosphate buffers and borate buffers.

EXAMPLES

Figure 1:
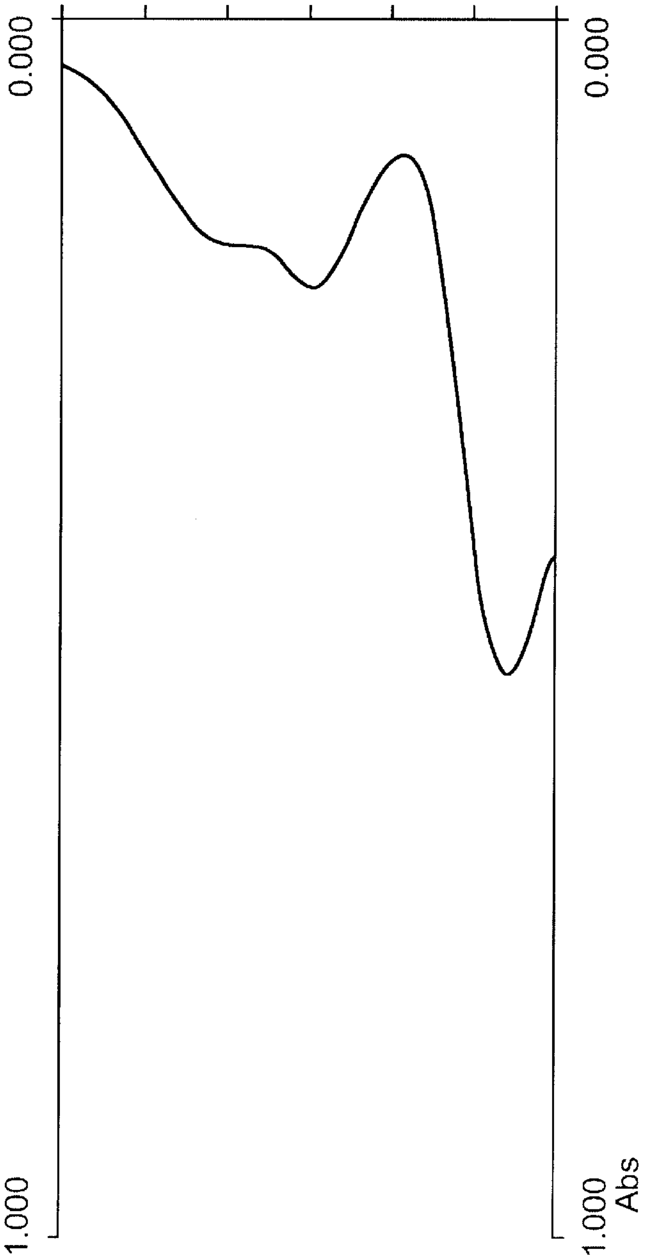
FIG. 1. UV spectrum of tetrodotoxin injection (990120-1A) identification.

The following examples illustrate the methods and compositions of the invention, but do not limit the invention, which is defined by the claims below.

Example 1

Formula Screening

This experiment mainly investigated the effects of various auxiliary solvents, various values of pH, temperature, light, oxygen, and buffer amounts on the stability of pharmaceutical solutions of tetrodotoxin (TTX). Consequently, an optimal composition of a TTX formulation is determined. The experiment results suggest a most preferred composition comprising dilute acetic acid as an auxiliary solvent, and 5% acetic acid-sodium acetate buffer solution as a stabilizer for the pH of the pharmaceutical solution of TTX. The optimal pH is in the range of 3.5–4.5. High temperature should be avoided. Sterilization should be performed in the process of formulation production. Excessive sunlight exposure should be avoided during transportation; and it is recommended that the finished product be stored in a cool place.

All the trial batches prepared following the formulation technology described above met the quality standards for injections in every test parameter. Their stability and reproducibility were good, indicating that this formulation design is appropriate and feasible.

1. Selection of Auxiliary Solvent:

Auxiliary solvents commonly used in formulation, dilute hydrochloric acid, dilute acetic acid, and citric acid solution, respectively, were tested for formulation of TTX for injection. The stability of TTX in these three acidic aqueous solutions is then compared by 100° C. water-bath acceleration tests.

Sample Preparation

Batch No. 1: TTX, dissolved in 0.01 N dilute hydrochloric acid, add water and prepare TTX solution to concentration of 12 μg/mL, adjust its pH about 4.4, fill and seal it into 2 mL ampoules.

Batch No. 2: TTX, dissolved in 0.5% dilute acetic acid, add pH 4.40 acetic acid-sodium acetate buffer solution, add water to prepare TTX solution at a concentration of 12 μg/mL, fill and seal it into 2 mL ampoules.

Batch No. 3: TTX, dissolved in 0.5% citric acid solution, add pH 4.40 citric acid-sodium citrate buffer solution, add water to prepare TTX solution at a concentration of 12 μg/mL, fill and seal it into 2 mL ampoules.

Test Method

Incubate the above samples in a 100° C. water-bath for acceleration experiments. Sample and determine the pH values and TTX content at 0 mm, 10 mm, 15 mm, 20 mm, 25 mm, 30 mm, and 60 mm. Results are shown in Table 1.

The rationale for choosing 100° C. water-bath acceleration experiment and sampling within 60 minutes to determine the pH values and TTX content is that the common process for sterile injection usually is to sterilize the formulation with 100° C. steam circulation for 15–30 minutes. When the experiment is carried out under these conditions, not only can the test results of formulation stability be obtained in shorter time, but also sterilizing conditions can be chosen properly.

TABLE 1

Changes of pH values and contents of various acidic aqueous solution (auxiliary solvent) of TTX in 100° C. water-bath

| Batch number | | Heating time (minutes) 0 (min) | 10 (min) | 15 (min) | 20 (min) Results | 25 (min) | 30 (min) | 60 (min) |
|---|---|---|---|---|---|---|---|---|
| (1) | PH | 4.70 | 4.77 | 4.82 | 4.86 | 5.02 | 5.11 | 5.20 |
| | Absolute content (μg/mL) | 11.32 | 8.07 | 7.40 | 7.02 | 6.47 | 6.37 | 5.48 |
| | Relative content (%) | 100 | 71.3 | 65.4 | 62.0 | 57.2 | 56.3 | 48.4 |
| (2) | PH | 4.45 | 4.45 | 4.45 | 4.44 | 4.43 | 4.44 | 4.46 |
| | Absolute content (μg/mL) | 12.93 | 10.15 | 9.16 | 8.88 | 7.97 | 7.76 | 7.28 |
| | Relative content (%) | 100 | 78.5 | 70.8 | 68.7 | 61.6 | 60.0 | 56.3 |
| (3) | PH | 4.77 | 4.75 | 4.75 | 4.72 | 4.73 | 4.75 | 4.73 |
| | Absolute content (μg/mL) | 13.35 | 8.85 | 7.23 | 7.25 | 6.59 | 6.64 | 6.20 |
| | Relative content (%) | 100 | 66.3 | 54.2 | 54.3 | 49.4 | 48.4 | 46.4 |

Discussion

As shown in Table 1, the three different formulation methods resulted in variation of their pH values. Upon heating at 100° C., the TTX content of all of the batches decreased. The pH of TTX hydrochloric acid solution changed considerably when no buffer solution was added. In the other two methods, the pH barely changed where dilute organic acids are used as auxiliary solvents and a buffer was added. Therefore, a certain amount of buffer solution must be added into the formulation in order to keep the pH constant. Table also shows that heating could cause a substantial decrease in TTX content. The degradation of sample (2) content is smaller than that of the other two samples, indicating that TTX is more stable in acetic acid solution.

2. Effects of Oxygen in Air and Heating at High Temperature on TTX Solution

According to the test results shown in Table 1, TTX contents of each batch dropped 20~35%, when heated at 100° C. for 10 min, indicating that heating at high temperature has great effects on TTX content. On the other hand, it was also necessary to determine whether or not the oxygen in air was one of the reasons that caused the TTX content to decrease substantially. Therefore, high-temperature acceleration tests of TTX solutions were carried out with and without de-oxygenating the preparation. Also, comparison was made with filling the ampoules with $N_2$ and $CO_2$, respectively.

Sample Preparation

Batch No. 1: TTX, dissolved in 0.5% dilute acetic acid, add acetic acid-sodium acetate buffer solution (pH 4.40), add water to prepare a TTX solution at a concentration of 12 μg/mL, fill and seal it into 2 ml ampoules (preparation without de-oxygenation).

Batch No. 2: TTX, formulated as above for Batch No. 1, but during the preparation, the water solution is de-oxygenated with $N_2$ first, then filled and sealed into 2 ml ampoules under $N_2$ (de-oxygenated preparation).

Batch No. 3: TTX, formulated as above for Batch No. 1, but in the process of formulation, the water solution is de-oxygenated with carbon dioxide ($CO_2$) first, then filled and sealed into 2 mL ampoules under $CO_2$ (de-oxygenated preparation).

Test Method

The batches were incubated in a 100° C. water-bath for acceleration experiments. Samples were taken and the pH values and TTX content were determined at 0 minutes, 10 minutes, 15 minutes, 20 minutes, 25 minutes, 30 minutes, and 60 minutes. The results are shown in Table 2.

TABLE 2

Test results of the effect of the oxygen in air and heating at high temperature (100° C.) on TTX solution

| Batch number | Heating time (minutes) 0 (min) | 10 (min) | 15 (min) | 20 (min) Results | 25 (min) | 30 (min) | 60 (min) |
|---|---|---|---|---|---|---|---|
| (1) Without deoxygenation | | | | | | | |
| PH | 4.45 | 4.45 | 4.45 | 4.44 | 4.43 | 4.44 | 4.46 |
| Absolute content (μg/mL) | 12.93 | 10.15 | 9.16 | 8.88 | 7.97 | 7.76 | 7.28 |
| Relative content (%) | 100 | 78.5 | 70.8 | 68.7 | 61.6 | 60.0 | 56.3 |
| (2) With $N_2$ | | | | | | | |
| PH | 4.58 | 4.57 | 4.58 | 4.58 | 4.50 | 4.49 | 4.48 |
| Absolute content (μg/mL) | 11.57 | 8.66 | 7.94 | 7.79 | 7.12 | 6.83 | 6.58 |
| Relative content (%) | 100 | 74.8 | 68.6 | 67.3 | 61.5 | 59.0 | 56.9 |
| (3) With $CO_2$ | | | | | | | |
| PH | 4.43 | 4.40 | 4.76 | 4.41 | 4.37 | 4.41 | 4.46 |
| Absolute content (μg/mL) | 10.95 | 8.33 | 7.91 | 7.07 | 6.56 | 6.48 | 6.31 |
| Relative content (%) | 100 | 76.1 | 72.2 | 64.6 | 59.9 | 59.2 | 57.6 |

Discussion

Based on the results shown in Table 2, there were no obvious differences in TTX content between the acceleration tests with de-oxygenation and without de-oxygenation, suggesting that the oxygen in air does not have any effect on TTX contents of the solutions. In these tests, when heated for 10 minutes at 100° C., TTX contents of all groups decreased by 25% on average, suggesting that heating at high temperature is the main cause for the decrease in TTX content of the solutions. Therefore, heating at high temperature should be avoided in the formulation process. It is recommended to use filtration sterilization instead of heat-sterilization.

3. Effects of Light on the Stability of TTX Solution

It is reported in the literature that TTX is relatively stable to light. The effects of light on its formulation are separately observed with diffusion light (indoor natural light) and direct irradiated sunlight.

Sample Preparation

Samples were prepared as described in section 1.

Test Method

Expose the samples to diffusion light and sunlight, respectively, for different periods; then examine the content changes. The results are shown in Table 3 and Table 4.

TABLE 3

Effects of diffusion light (indoor natural light) on TTX solution

| Content | Time 0 d | 7 d | 14 d Results | 21 d |
|---|---|---|---|---|
| Absolute content (μg/mL) | 12.93 | 12.95 | 12.92 | 12.84 |
| Relative content (%) | 100 | 100 | 99.9 | 99.3 |

TABLE 4

Effects of direct irradiated sunlight on TTX solution

| Content | Time 0 h | 1 hr | 2 hr Results | 3 hr |
|---|---|---|---|---|
| Absolute content (μg/mL) | 12.93 | 12.77 | 12.61 | 12.55 |
| Relative content (%) | 100 | 98.8 | 97.5 | 97.1 |

Discussion

Table 3 and Table 4 show that the test results are in accordance with those reported in the literature. TTX solution is relatively stable to light, thus there is no need to protect the product from light. When exposed directly to sunlight, however, the content changed slightly, suggesting that excessive exposure to sunlight should be avoided and the formulation should be stored in cool and shaded places.

4. Observation of the Stability of TTX Solutions at Various pH

It was reported in the literature that TTX is relatively stable in acidic and neutral us solution. TTX stability is examined at different pH.

Sample Preparation:

TTX solutions containing various amounts of buffer to reach pH values of 3.00, 3.50, 4.00, 4.50, 5.00, 5.50, respectively, were prepared. TTX was dissolved in 0.5% dilute acetic acid, add required amount of acetic acid-sodium acetate buffer solutions to obtain the pH values above, add water and prepare TTX solution with a concentration of 12 μg/mL, fill and seal into 2 mL ampoules.

Test Method:

Samples were incubated at 70° C. Samples were drawn and the TTX content was measured at 0, 0.5, 1, 2, 4, 8 hours, respectively. The results are listed in Table 5.

TABLE 5

Acceleration test results of TTX solutions of various pH values at constant temperature (70° C.)

| | pH | | | | | | | | | | | |
|---|---|---|---|---|---|---|---|---|---|---|---|---|
| | 3.00 | | 3.48 | | 4.08 | | 4.50 | | 5.02 | | 5.50 | |
| | Results | | | | | | | | | | | |
| Time (Hr) | Absolute content (μg/mL) | Relative content (%) | Absolute content (μg/mL) | Relative content (%) | Absolute content (μg/mL) | Relative content (%) | Absolute content (μg/mL) | Relative content (%) | Absolute content (μg/mL) | Relative content (%) | Absolute content (μg/mL) | Relative content (%) |
| 0 | 12.50 | 100 | 12.19 | 100 | 11.12 | 100 | 11.38 | 100 | 12.13 | 100 | 12.02 | 100 |
| 0.5 | 12.27 | 98.2 | 11.88 | 97.5 | 10.99 | 98.8 | 10.94 | 96.1 | 11.56 | 95.3 | 10.34 | 86.0 |
| 1 | 12.21 | 97.7 | 11.73 | 96.2 | 10.74 | 96.5 | 10.62 | 93.3 | 10.85 | 89.4 | 9.65 | 80.3 |
| 2 | 11.55 | 92.4 | 11.51 | 94.4 | 10.33 | 92.9 | 9.94 | 87.3 | 10.09 | 83.2 | 9.36 | 77.9 |
| 4 | 11.14 | 89.1 | 10.99 | 90.2 | 9.48 | 85.2 | 9.38 | 82.4 | 9.87 | 81.4 | 8.48 | 70.6 |
| 8 | 10.80 | 86.4 | 10.15 | 83.3 | 8.73 | 78.5 | 7.96 | 69.9 | 8.23 | 67.8 | 7.21 | 60.0 |

Discussion:

The test results indicated pH-dependent degradation of the TTX solution. The degradation is greater at higher pH. TTX is relatively more stable with pH in the range of 3.00–4.08.

5. Selection of the Added Amount of Acetate Buffer

As shown in the above tests, the degradation rate of a warmed TTX solution is higher with increasing pH. Therefore, for the formula design, the pH of TTX injection should be assigned to the partial acidic range, and an adequate amount of buffer solution should be added. In this way, a relatively constant pH environment for the formulation can be maintained so as to ensure stability of the formulation during a designated storage period. Hence, we applied the orthogonal method to design the adding amount of acetate buffer solutions of various pH values for the tests.

Experiment Design

The pH values of acetate buffer solutions and their respective adding amounts are optimized by way of orthogonal test design. The selected and used factors and their levels for the tests are listed in the following Table 6.

TABLE 6

Factors and levels

| | Factor | |
|---|---|---|
| Level | A pH | B Adding amount of buffer solutions (based on the total volume of the prepared solutions) |
| 1 | 3.0 | 0.1% |
| 2 | 3.5 | 1% |
| 3 | 4.5 | 5% |
| 4 | 5.0 | |

Test Method

According to the orthogonal test design, select acetate buffer solutions of various pH values and related adding amount to prepare samples. Following the selected test conditions as described in section 4, heat the samples in 70° C. water-bath for 2 h; then examined TTX contents in the samples, and calculate the residual rates. The results are listed in Table 7.

TABLE 7

The arrangement of orthogonal experiments and analysis of results

| | Column number of factor design | | | | | |
|---|---|---|---|---|---|---|
| Test sample | A | B | A × B | | | Test results $Y_j$ |
| number | 1 | 2 | 3 | 4 | 5 | Residue % |
| 1 | 1 | 1 | 1 | 1 | 1 | 88.5 |
| 2 | 1 | 2 | 2 | 2 | 2 | 90.6 |
| 3 | 1 | 3 | 3 | 3 | 3 | 95.5 |
| 4 | 2 | 1 | 2 | 3 | 3 | 92.6 |
| 5 | 2 | 2 | 1 | 1 | 2 | 97.0 |
| 6 | 2 | 3 | 3 | 2 | 1 | 97.9 |
| 7 | 3 | 1 | 3 | 3 | 2 | 89.0 |
| 8 | 3 | 2 | 1 | 2 | 1 | 90.9 |
| 9 | 3 | 3 | 2 | 1 | 3 | 90.1 |
| 10 | 4 | 1 | 3 | 2 | 3 | 83.1 |
| 11 | 4 | 2 | 2 | 1 | 1 | 85.3 |
| 12 | 4 | 3 | 1 | 3 | 2 | 84.5 |
| $I_j$ | 274.6 | 352.2 | 360.9 | 360.9 | 362.6 | |
| $II_j$ | 287.5 | 363.8 | 358.6 | 362.5 | 361.1 | |
| $III_j$ | 270.0 | 368.0 | 365.5 | 361.6 | 361.3 | $\sum_{j=1}^{12} yj = 1085.0$ |
| $IV_j$ | 252.9 | | | | | |
| $I_j$ | 91.5 | 88.3 | 90.2 | 90.2 | 90.6 | |
| $II_j$ | 95.8 | 91.0 | 89.6 | 90.6 | 90.3 | |
| $III_j$ | 90.0 | 92.0 | 91.4 | 90.4 | 90.3 | $(y_i)^2 = 98102.08$ |
| $IV_j$ | 84.3 | | | | | |
| R | 11.5 | 3.7 | 1.8 | 0.4 | 0.3 | 12 |
| $SS_j$ | 204.53 | 29.09 | 6.18 | 0.32 | 0.34 | |

TABLE 8

Analysis of variance

| Variance source | Sum of squares | Degree of freedom | Variance | F value | Significance |
|---|---|---|---|---|---|
| A | $SS_A$ = 319.98 | 3 | $SS_A/3$ = 106.66 | $F_A$ = 28.52 | □ □ |
| B | $SS_B$ = 133.38 | 2 | $SS_B/2$ = 66.69 | $F_B$ = 17.83 | □ □ |

TABLE 8-continued

| Analysis of variance | | | | | |
|---|---|---|---|---|---|
| Variance source | Sum of squares | Degree of freedom | Variance | F value | Significance |
| Error | $SS_e$ = 22.44 | 6 | $SS_e/6$ = 3.74 | | |
| Sum | SS = 475.80 | 11 | | | |

$F_{0.05}$ (3,6)=4.76, $F_{0.01}$ (3,6)=9.78, $F_{0.05}$ (2,6)=5.14, $F_{0.01}$ (2,6)=10.92

Discussion

Based on the test results and the analysis of the variance table, factor A and factor B were found to be significantly different (P<0.01), indicating that the pH value of the acetate buffer and the added amount of buffer have substantial effects on the stability of the formulation. Based on the test results, the best combination is $A_2B_3$, i.e. the highest stability of TTX solution is achieved when pH is 3.5 and the amount of buffer added is 5%.

From the above experiments, the preferred TTX formulation comprises dilute acetic acid as an auxiliary solvent, and 5% acetic acid-sodium acetate buffer of pH in the range from 3.5 to 4.0. Heating at high temperature should be avoided in the formulation manufacturing process, so it is recommended to use sterile preparation or filtration of the finished formulation for sterilization. Exposure to direct sunlight should be avoided during transportation. It is recommended that the finished product be stored in a cool place.

All trial products prepared with the above formulation technique met the quality requirements for pharmaceutical injections after being examined in all criteria, and displayed fine reproducibility and stability.

TABLE 9

| Sources and quality standards of the raw and auxiliary materials | | | |
|---|---|---|---|
| Name | Specification | Quality standard | Manufacturer |
| TTX | | Manufacturer's standard | Nanning Maple Leaf Pharmaceutical Co., Ltd |
| Acetic acid | Pharmaceutical | Pharmacopoeia of P. R. China, Vol. 2, 1995:1064 | Nanning No 2 Chemical Factory |
| Sodium acetate | AR | National standard GB 694 = 81 | Guangzhou No 2 Chemical Reagent Factory |

REFERENCES

[1] Dianzhou Bi, Pharmaceutics, $4^{th}$ edition, pp 271–272, People's Health Publishing Services.

[2] Maoqin Zhou et al, A method of extracting tetrodotoxin with high yield□Chinese patent application no. 00124517.1 □ Sep. 18, 2000.

[3] Qingbin Dong, A method of analgesia by systemic administration□Chinese patent application no. 00124516.3 □ Sep. 18, 2000.

Example 2

Quality Study of Tetrodotoxin Formulation

1. Properties

This product is a colourless, clear liquid.

| Batch number | Properties |
|---|---|
| 990120-1A | Colourless, clear liquid |
| 990121-2A | Colourless, clear liquid |
| 990122-3A | Colourless, clear liquid |

Conclusion: All the Samples of the Three Batches are Colourless, Clear Liquid.

2. Identification 2.1 UV Absorbance: Tetrodotoxin itself has no characteristic UV absorbance. However, it can be hydrolyzed with alkaline water and produce 2-amino-6-methylol-8-hydroxyquinazoline ($C_9$ base), and a certain amount of sodium oxalate, which shows significant characteristic absorbance in the UV region and thus can be used for identification purposes.

Figure 2:
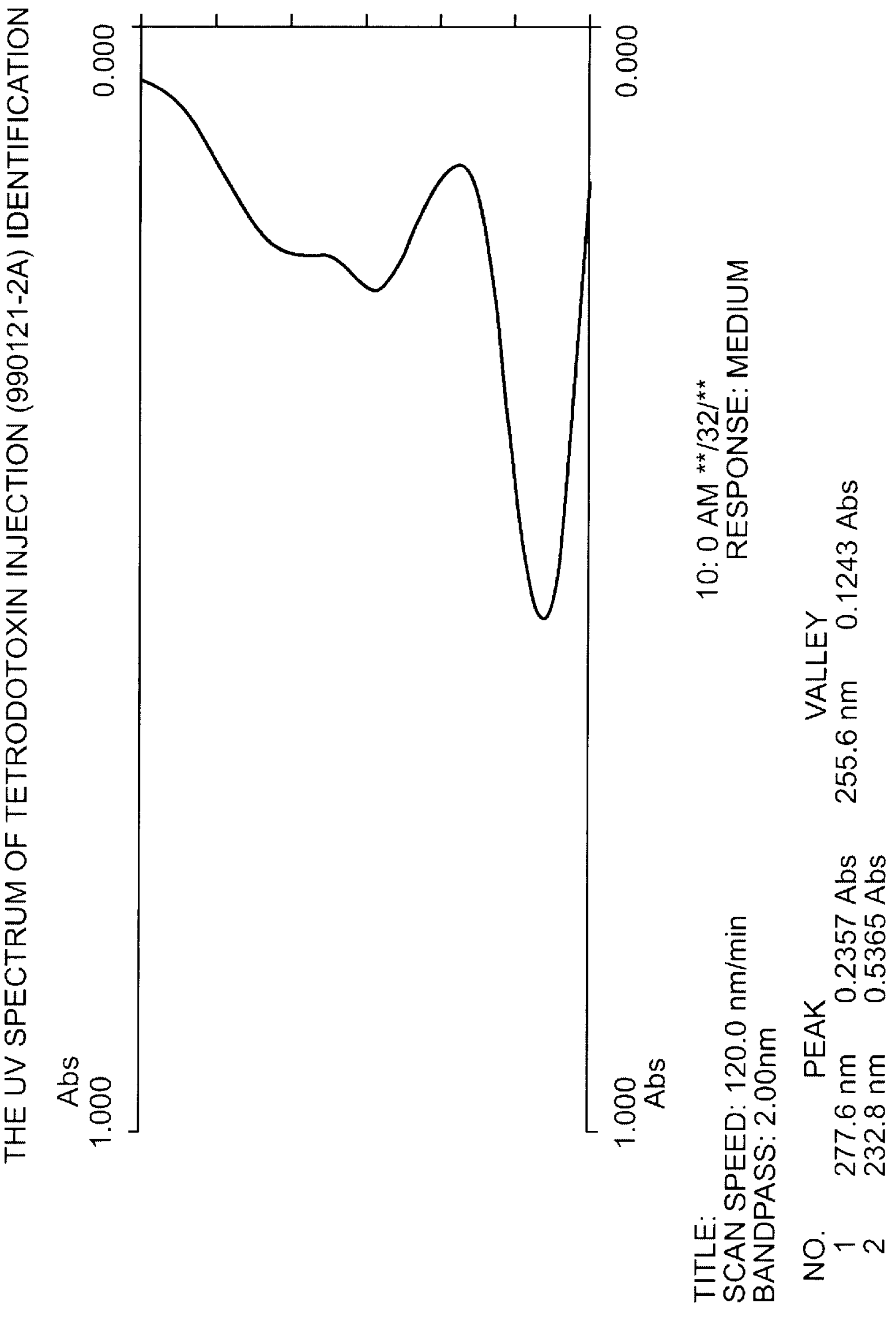
FIG. 2. UV spectrum of the tetrodotoxin control sample (S-1) identification.

Method: Take 10 mL of product and put into a test tube with stopper, add 1.0 mL of 6.0M NaOH solution, shake and mix well, and heat for 45 minutes in 80 ° C. water-bath, then cool down to room temperature immediately, and measure its absorbance spectrum in the range of 340–220 nm according to the spectrophotometry method listed in Appendix IV A, Pharmacopoeia of P. R. China, Vol. 2, 1995. (Results are shown in FIGS. 1 and 2 and in the Table below).

| Batch number | λmax (nm) | | λmin (nm) |
|---|---|---|---|
| Control sample | 277.5 | 230.8 | 255.7 |
| 990120-1A | 277.1 | 232.3 | 255.1 |
| 990121-2A | 277.6 | 232.8 | 255.6 |
| 990122-3A | 277.0 | 232.0 | 254.2 |

Figure 3:
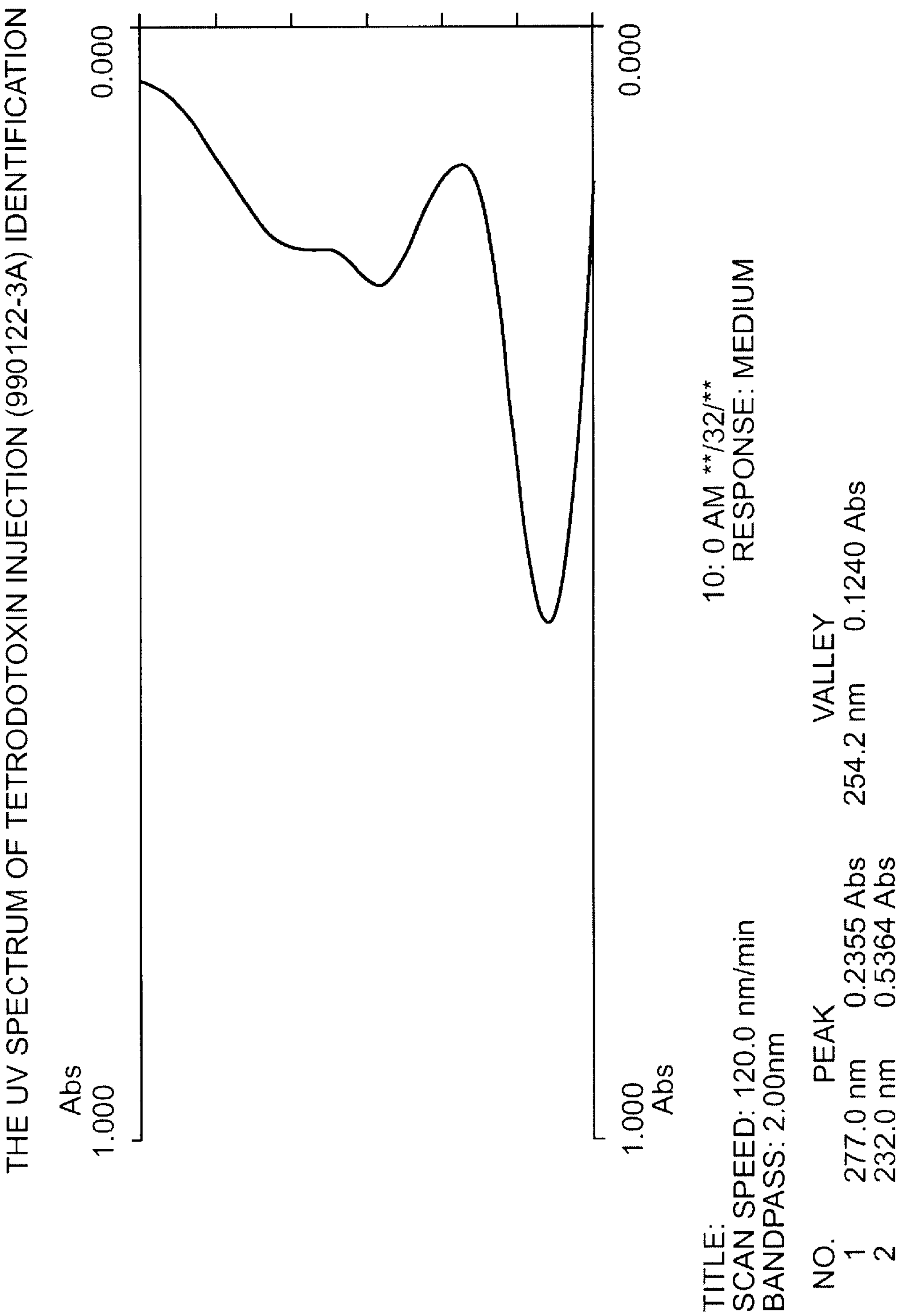
FIG. 3. chromatogram of the retention time of three batches of tetrodotoxin and a control sample.

2.2 HPLC: HPLC was performed as described for "content determination" below. The chromatogram is shown in FIG. 3. The product sample and the control sample show the same retention time.

| Batch number | $t_R$ (min) |
|---|---|
| Control sample | 16.8 |
| 990120-1A | 16.7 |
| 990121-2A | 16.6 |
| 990122-3A | 16.6 |

3. Inspection 3.1 Acidity:

The pH of the sample solutions.

| Batch number | PH |
|---|---|
| 990120-1A | 3.9 |
| 990121-2A | 3.9 |
| 990122-3A | 3.9 |

Conclusion: The pH values of the three batches of the samples are all 3.9.

3.2 Clarity of Solution:

Take 200 ampoules from each of the three batches, examine for clarity against the "Clarity Inspection Procedures and Standards". The results are listed below:

| Batch number | Clarity |
|---|---|
| 990120-1A | Clear |
| 990121-2A | Clear |
| 990122-3A | Clear |

Conclusion: The samples of the three batches are all clear.

3.3 Solution Transmittancy:

The transmittancy of the samples from the three batches is measured at 430 nm as per the Spectrophotometry method (Pharmacopoeia of P. R. China, Appendix IV A, Vol. 2, 1995). The results are listed as follows:

| Batch number | Transmittancy |
|---|---|
| 990120-1A | 98.9 |
| 990121-2A | 100.1 |
| 990122-3A | 99.8 |

Conclusion: The light transmittances of the three batches of samples are all greater than 98%.

3.4 Loading Amount:

Take 5 ampoules from each of the three batches, check their loading amounts as per the inspection method for injection loading amount listed in Appendix I B, Pharmacopoeia of P. R. China, Vol. 2, 1995. The results are as follows:

| Batch number | Amount of package (mL) |
|---|---|
| 990120-1A | 2.10, 2.16, 2.20, 2.22, 2.22 |
| 990121-2A | 2.38, 2.32, 2.38, 2.36, 2.34 |
| 990122-3A | 2.32, 2.36, 2.34, 2.40, 2.36 |

Conclusion: The loading amounts of these samples are all more than the labelled amount of 2.0 mL.

3.5 Sterilization:

Take the product and inspect it according to the method listed in Appendix XI H, Pharmacopoeia of P. R. China, Vol. 2, 1995. The product meets the criteria.

3.6 Bacteria Endotoxin:

Take the product and check according to the method listed in Appendix XI E, Pharmacopoeia of P. R. China, Vol. 2, 1995. The content of the bacteria endotoxin is less than 7.5 EU/mL.

3.7 Abnormal Toxicity:

Take the product and dilute it as 1:75 ratio, inspect it according to the method listed in Pharmacopoeia of P. R. China, Appendix XI C, Vol. 2, 1995. The results meet the criteria.

3.8 Hypersensitivity Test:

Method: A group of 6 guinea pigs, half male and half female, were each given 0.5 mL TTX injection intraperitoneally once every other day, a total of three doses per animal. Fourteen days after the last dose, three animals of the group were each given 1.5 mL test drug intravenously to test for hypersensitivity reactions. The animals were observed closely in the following 15 minutes to 24 hours for hypersensitivity reactions. Positive hypersensitivity reactions were concluded if two or more of the following clinical signs were observed: pilo-erection, dyspneic respiration, sneezing, retching and coughing. Hypersensitivity was also concluded if any of rale, twitching or death from collapse were observed. Otherwise, negative reactions were concluded. Twenty one days after the last dose, the remaining three animals were tested by the same method, and their reactions were determined by the same criteria.

3.9 Impurities:

According to the method in"content determination" below, accurately weigh a proper amount of the product, add water to make a control solution with a concentration of 0.75 μg/mL. Take 100 μl of this control solution and inject into the chromatograph for preliminary testing. Adjust the detection sensitivity so that the peak height of the major component is 10–25% of the full scale. Accurately take 100 μl of the product and inject into the chromatograph, record the chromatogram over twice the retention time of the major component. Measure the sum of the impurity peaks, which should not be greater than the peak area of the major component.

| Batch number | Related substance (%) |
|---|---|
| 990120-1A | Not greater than the major component peak area |
| 990121-2A | Not greater than the major component peak area |
| 990122-3A | Not greater than the major component peak area |

4. Content Determination

HPLC assay is used as the analysis method f or content determination.

4.1 Instrument and Reagents

Instrument: Beckman HPLC (U.S.A., including Model 125 pump. Model 166 variable wavelength detector and Gold Nouveau chromatography workstation).

Pharmaceutical: Tetrodotoxin, refined by Nanning Maple Leaf Pharmaceutical Co., Ltd. (MLP); and the control sample of TTX, provided by MLP.

Reagents: Sodium 1-Heptanesulfonate (Tokyo Kasei Kogyo Co., Ltd. Japan), methanol (Merck), de-ionized water.

4.2 Chromatographic Conditions and System:

Column: ODS (5 μm), 4.6 mm×250 mm

Column temperature: 30 ° C.

Mobile phase: 0.01M Sodium 1-Heptanesulfonate (pH 5.30)-Methanol (100:1)

Flow rate: 1.5 mL/min

Detection wavelength: 205 nm

Figure 4:
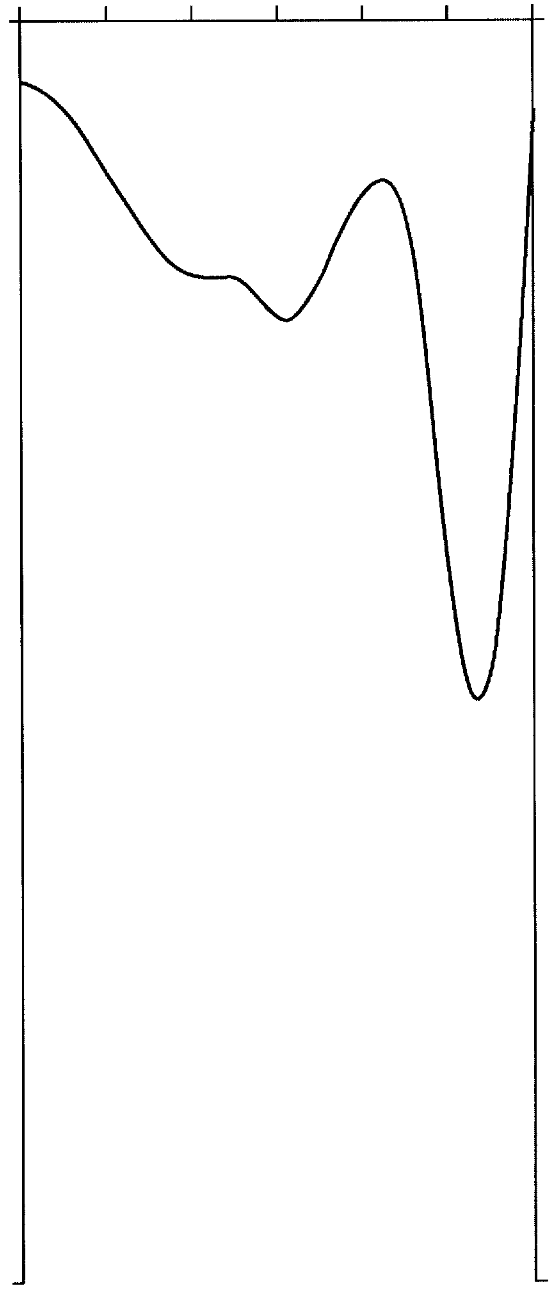
FIG. 4. HPLC chromatogram of a content determination of a sample of a tetrodotoxin injection formulation (990120-1A).

The chromatogram is shown in FIG. 4.

Column efficiency (n)

Calculated it as tetrodotoxin peak, n=43227 theoretical plates/meter

Separation of tetrodotoxin peak and its adjacent peaks (R)=1.8

Asymmetric factor for tetrodotoxin peak (T)=1.14

4.3 Precision

Inject 100 μl of the sample solution into the chromatograph, record chromatogram and measure the peak area, repeat the assay six times. The RSD of the tetrodotoxin peak area is 0.2% (n=6).

4.4 Linear Range and Minimum Detection Limit

Accurately weigh 13.90 mg of the TTX control sample and put into a 100 ml volumetric flask, add 0.02% acetic acid solution and dilute to mark, shake and mix well. Precisely inject 80, 40, 20, 8, and 4 μl of the solution into the chromatograph and record their chromatogram, respectively.

Use the peak area as the vertical axis and the sampling amount as the horizontal axis to plot the standard calibration curve. The linear regression equation is y=3403.91+243226×with a linear range of 12.625~0.505 μg and a correlation coefficient of 0.9999.

The minimum detection limit is 0.01 ng based upon the signal to noise ratio (S/N≧3).

4.5 Recovery Test:

Formula:

| | |
|---|---|
| Tetrodotoxin | 15 mg |
| 0.2% acetic acid solution | 1 mL |
| pH 3.5 acetic acid-sodium acetate solution | 5% (50 mL) |
| Water for injection | add to 1000 mL |

Method: Prepare a solution without tetrodotoxin according to the above formula, called solution A.

Weigh 14.08 mg tetrodotoxin and add 0.2% acetic acid to make 50 mL of solution.

This solution is called solution B.

Take 0.5 mL of solution B and add 0.2% acetic acid solution to make 10 mL. This solution is called solution C.

Take 0.5 mL of solution B and add solution A to make 10 mL. This solution is called solution D.

Figure 5:
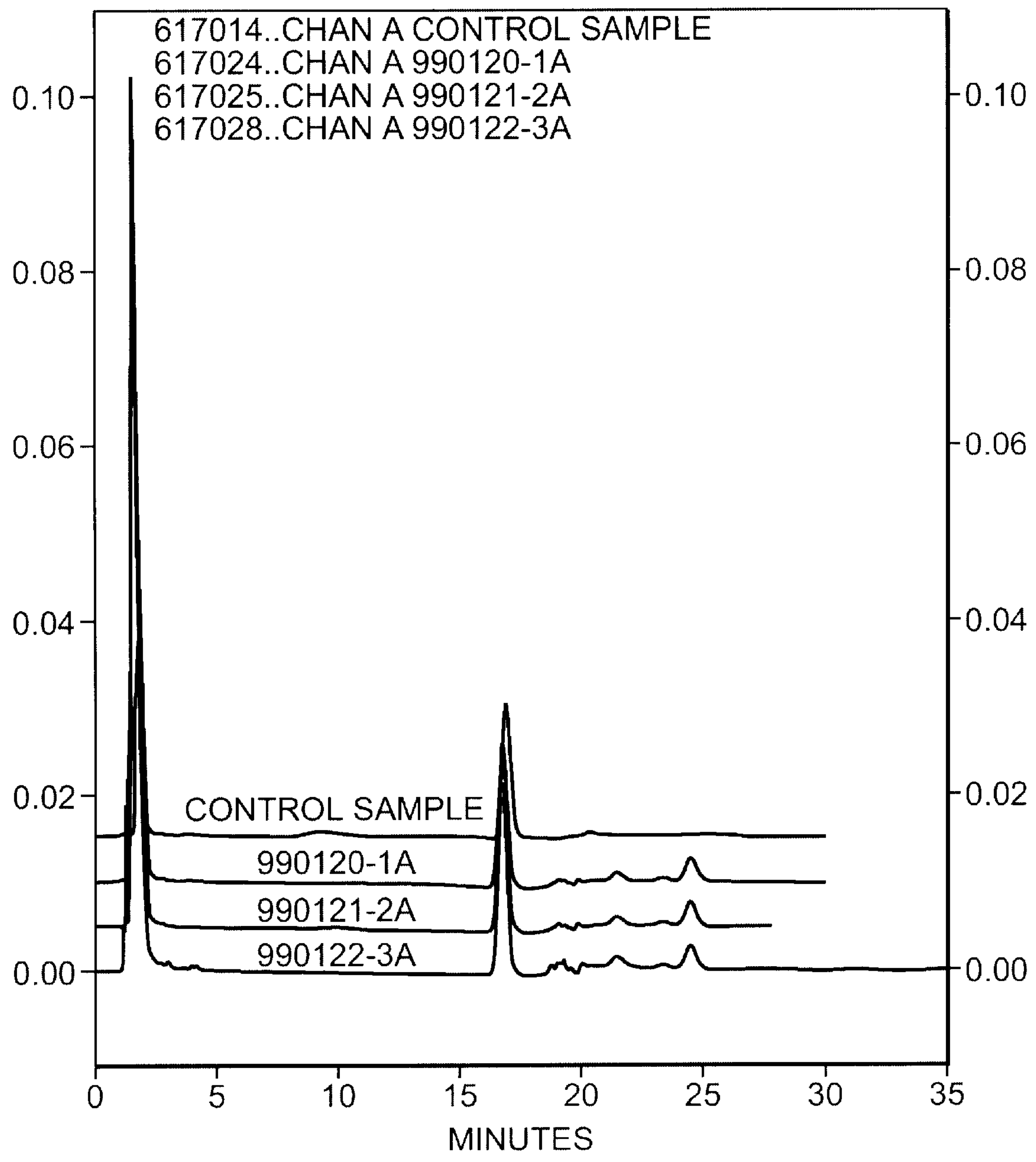
FIG. 5. HPLC chromatogram of a recovery test of a sample of a tetrodotoxin injection formulation.
Figure 6:
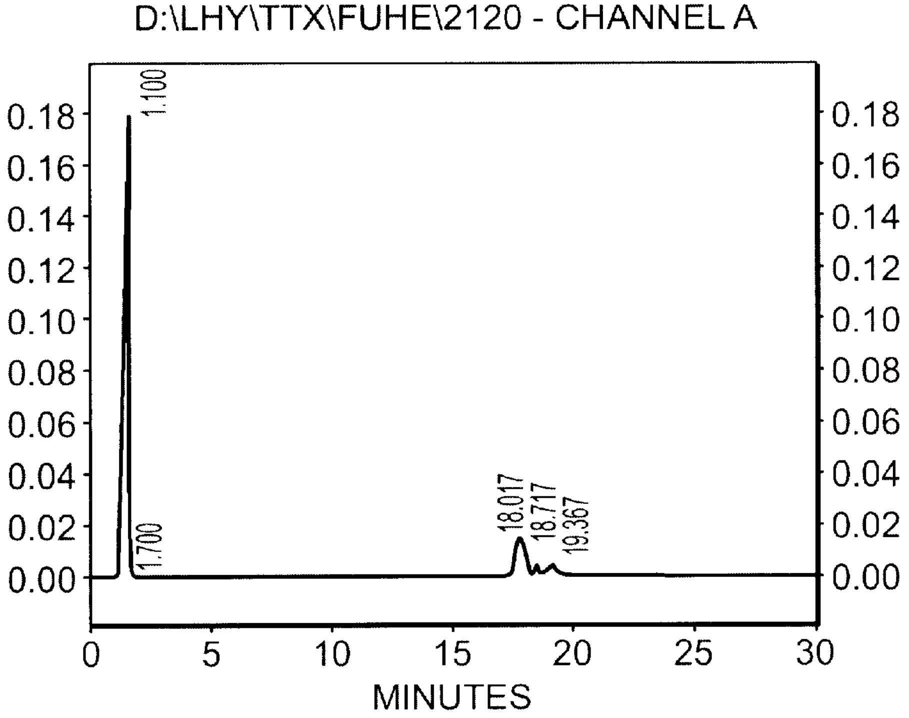
FIG. 6. Day 0 chromatogram of TTX injection samples (Batch 990120-1A).
Figure 7A:
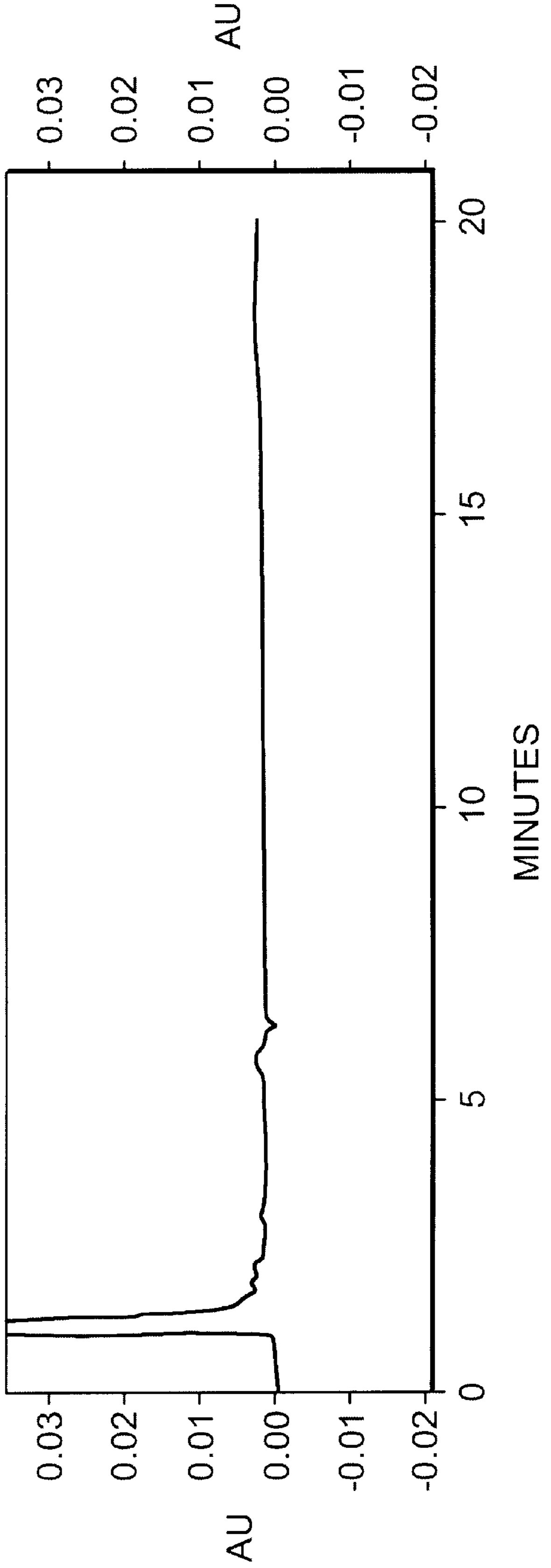
FIG. 7. Chromatogram of a sample of a TTX injection formulation (Batch 990120-1A) exposed to fluorescent light for 5 days.
Figure 7B:
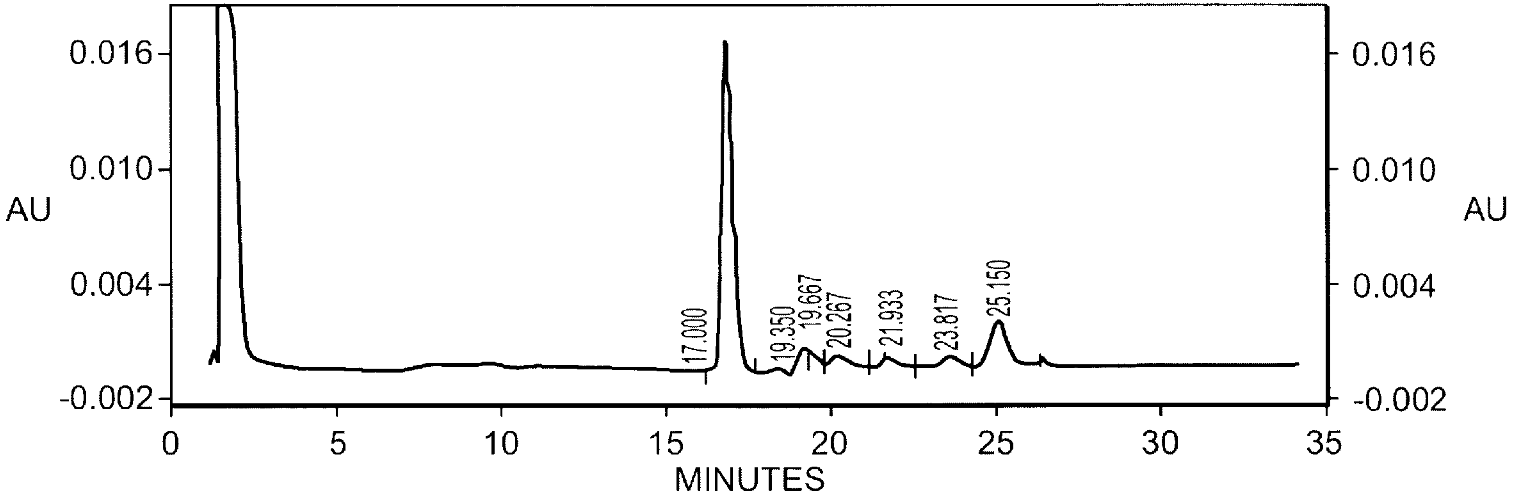
Figure 7C:
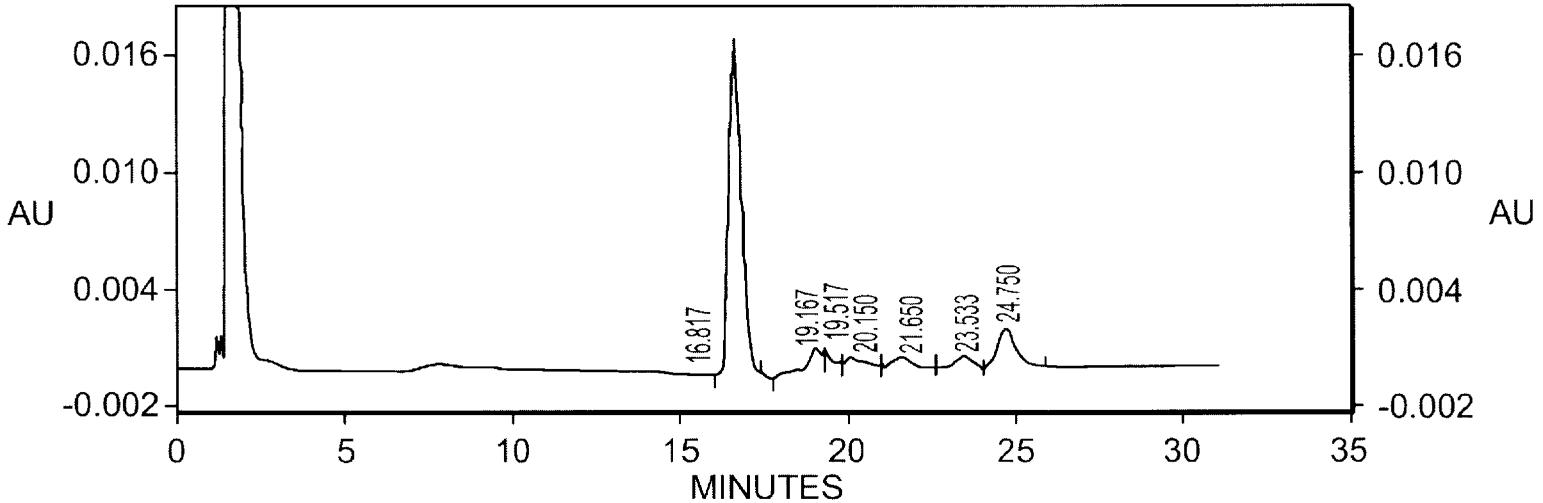
Figure 8:
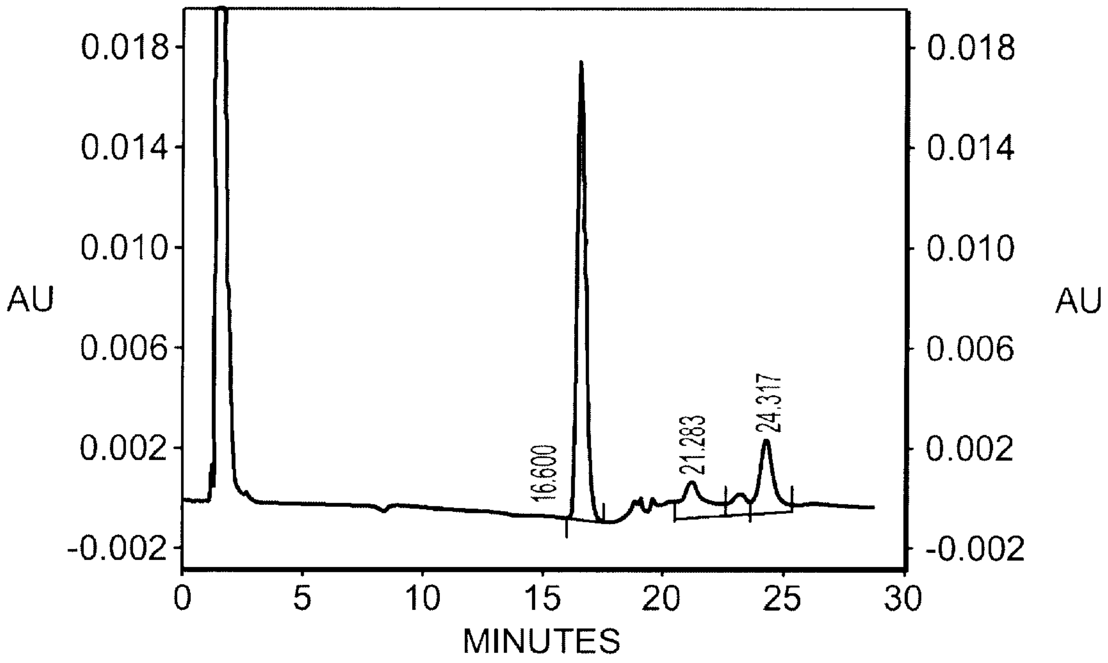
FIG. 8. Chromatogram of a sample of a TTX injection formulation (Batch 990120-1A) exposed to fluorescent light for 10 days.
Figure 9:
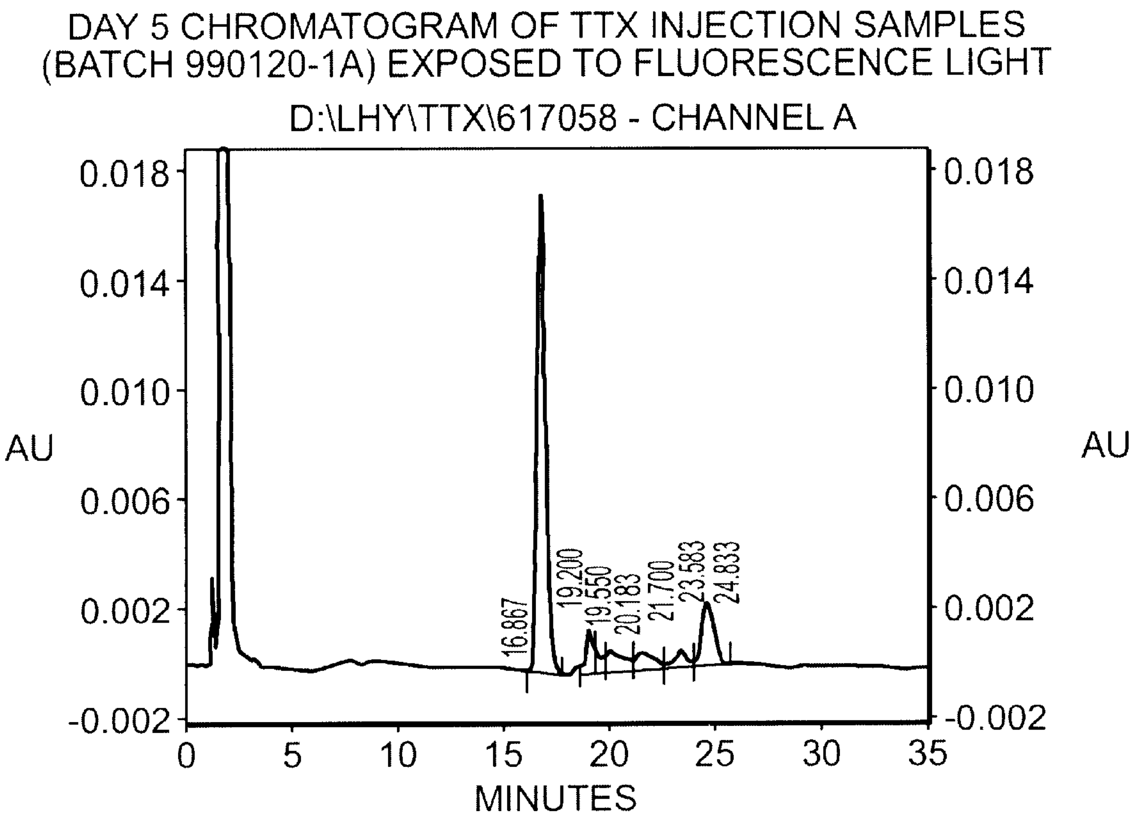
FIG. 9. Chromatogram of a sample of a TTX injection formulation (Batch 990120-1A) stored at 40° C. for 5 days.
Figure 10:
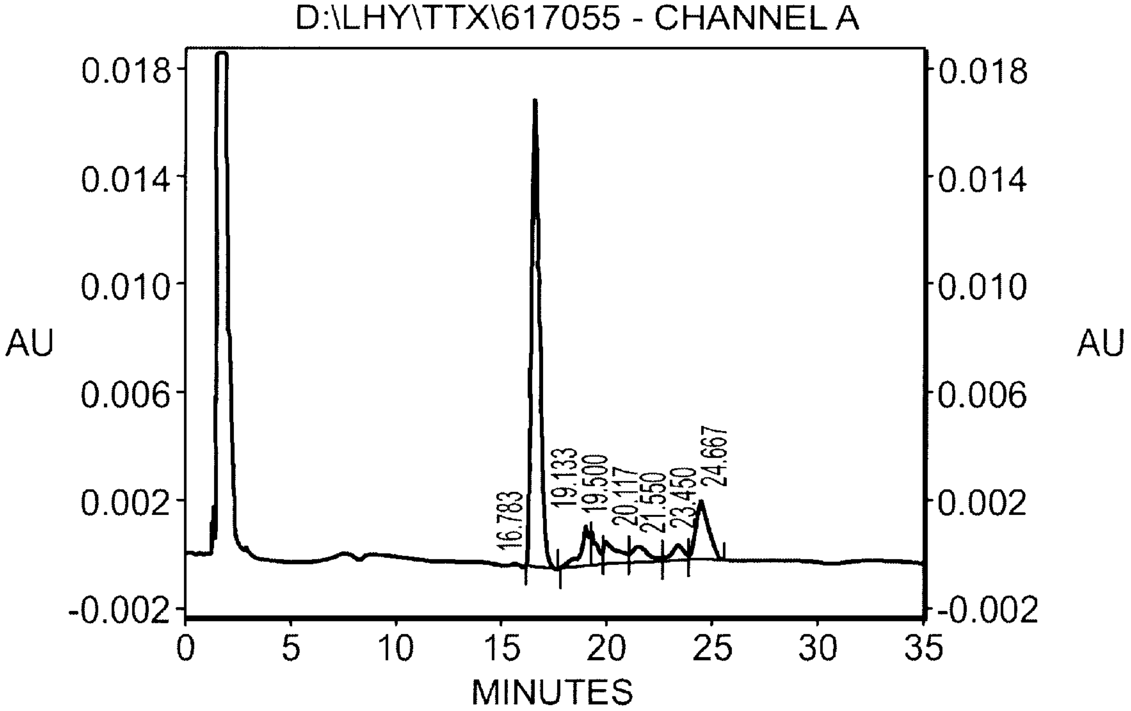
FIG. 10. Chromatogram of a sample of a TTX injection formulation (Batch 990120-1A) stored at 40° C. for 10 days.
Figure 11:
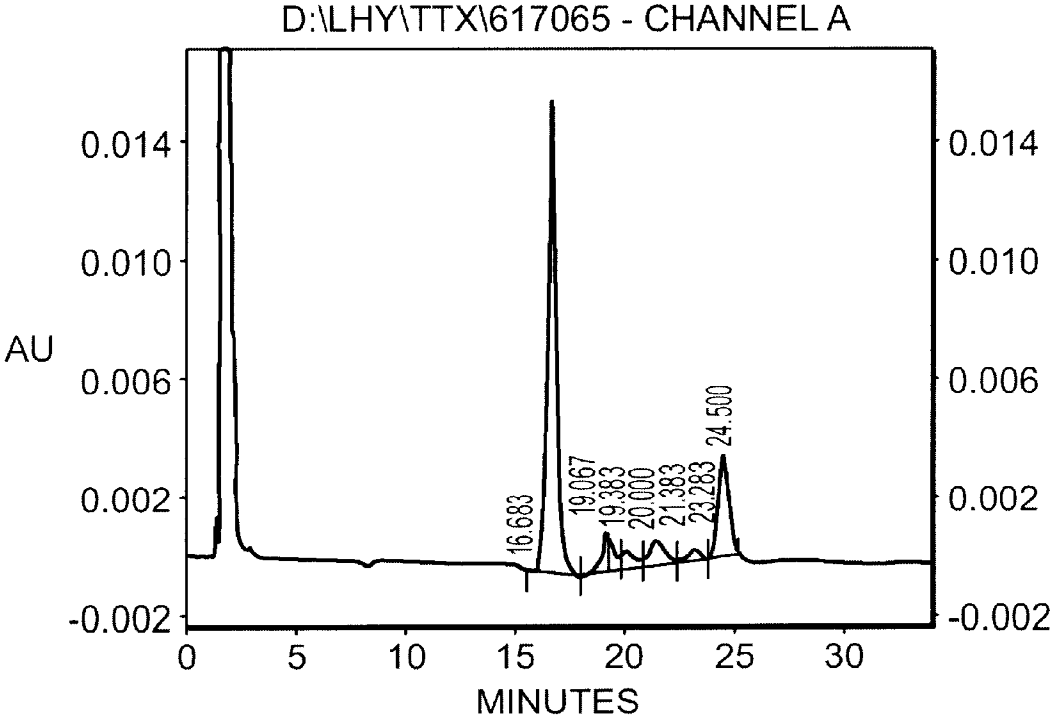
FIG. 11. Chromatogram of a sample of a TTX injection formulation (Batch 990120-1A) stored at 60° C. for 5 days.
Figure 12:
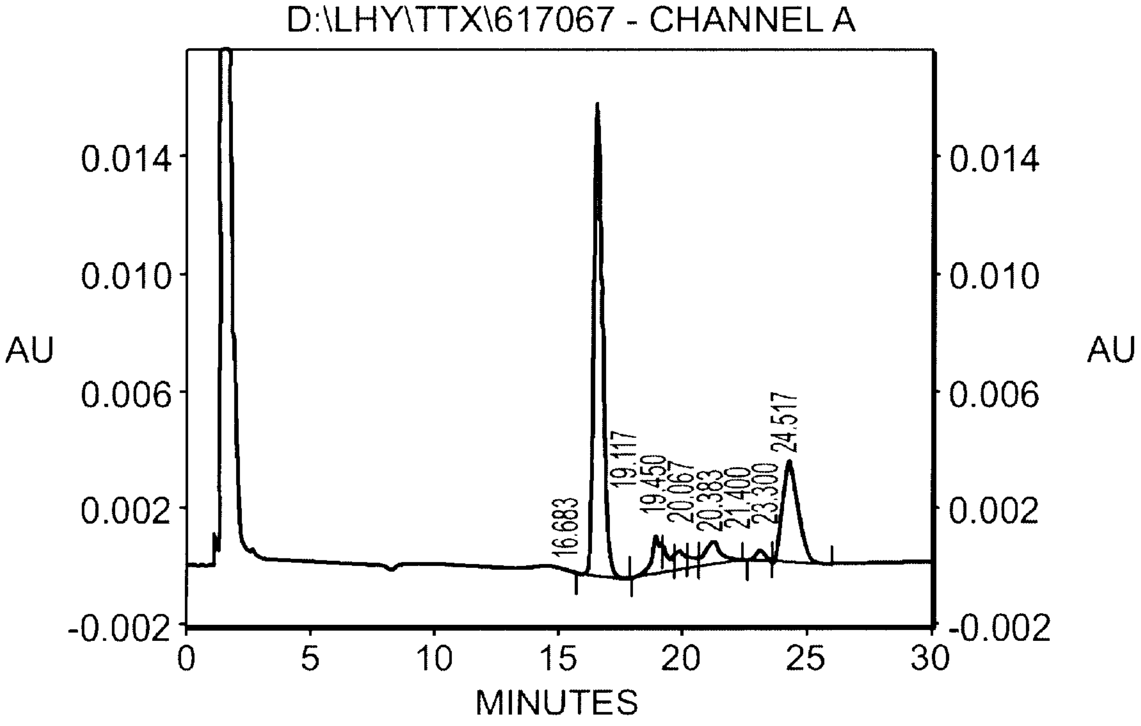
FIG. 12. Chromatogram of a sample of a TTX injection formulation (Batch 990120-1A) stored at 60° C. for 10 days.
Figure 13:
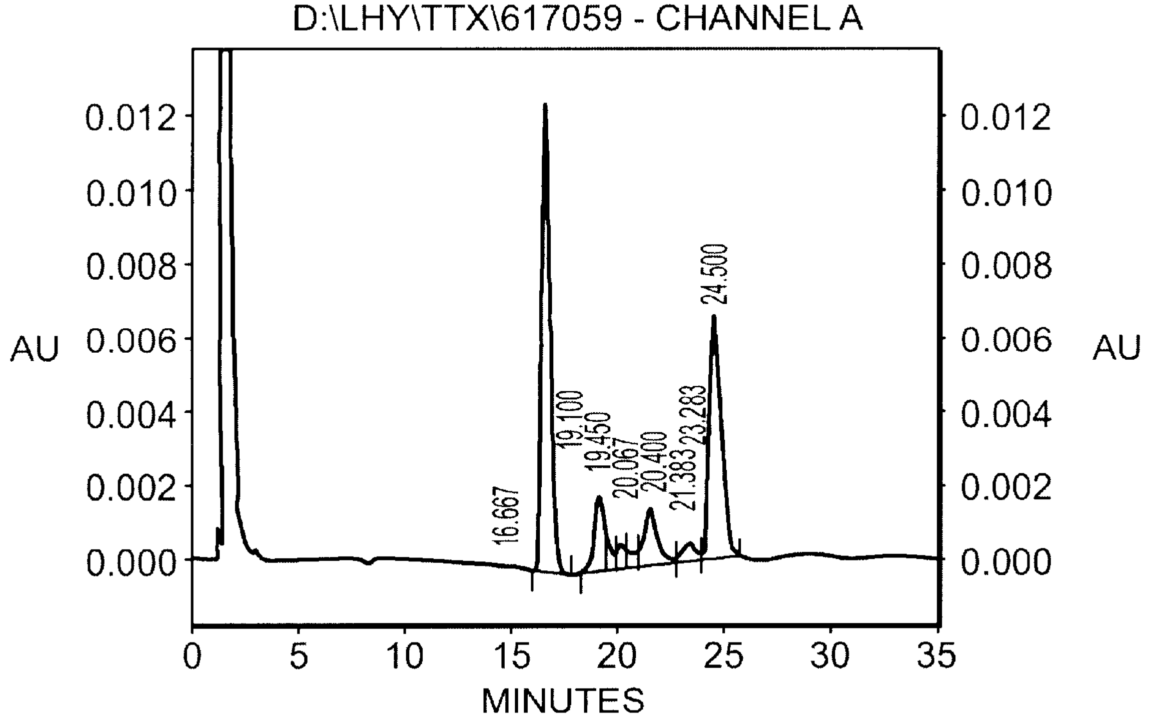
FIG. 13. Chromatogram of a sample of a TTX injection formulation (Batch 990120-1A) stored at 80° C. for 5 days.
Figure 14:
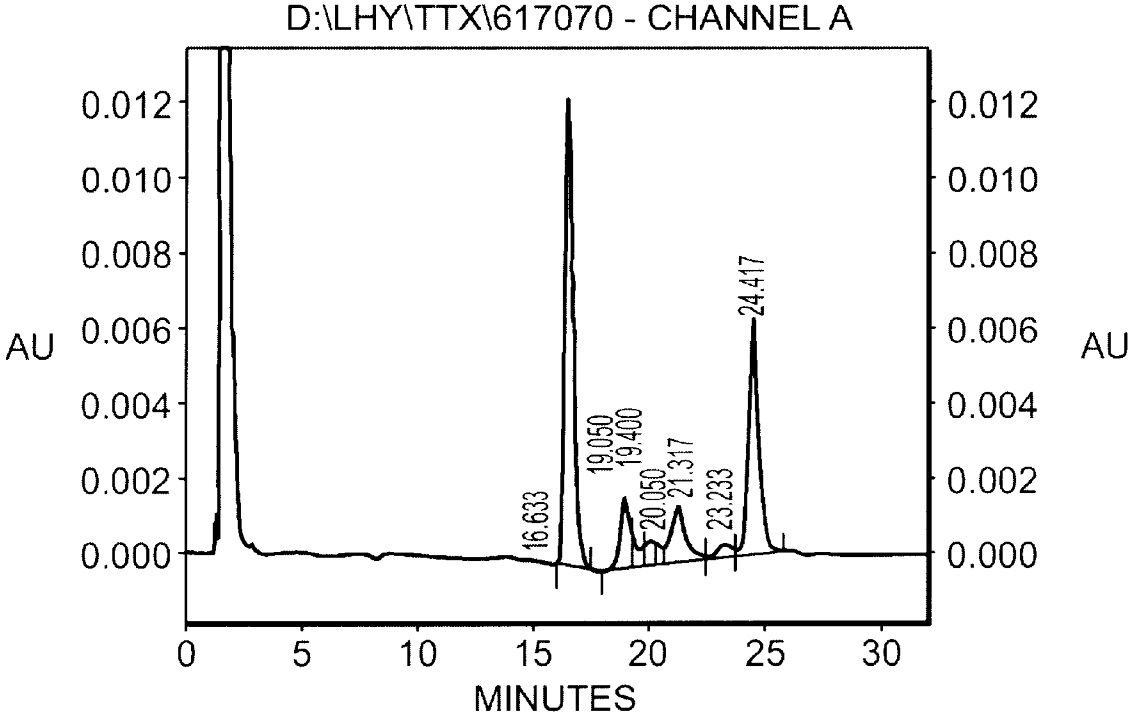
FIG. 14. Chromatogram of a sample of a TTX injection formulation (Batch 990120-1A) stored at 80° C. for 10 days.
Figure 15:
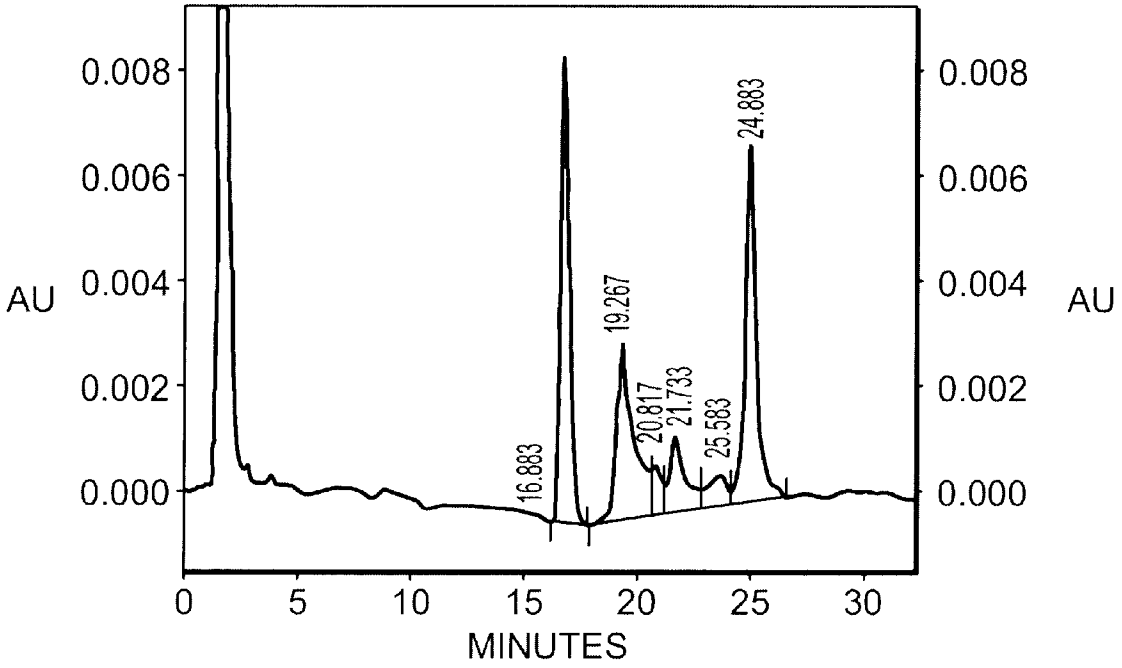
FIG. 15. Month 1 chromatogram of a sample of a TTX injection formulation (Batch 990120-1A) in acceleration test at 40° C.
Figure 16:
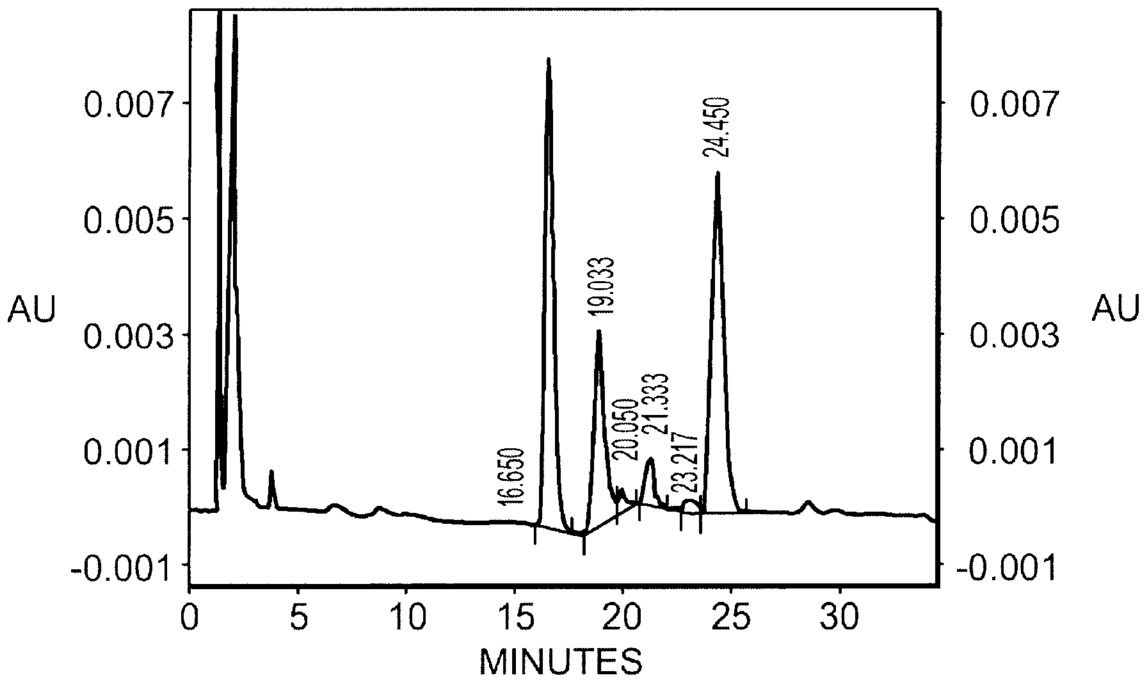
FIG. 16. Month 2 chromatogram of a sample of a TTX injection formulation (Batch 990120-1A) in acceleration test at 40° C.
Figure 17:
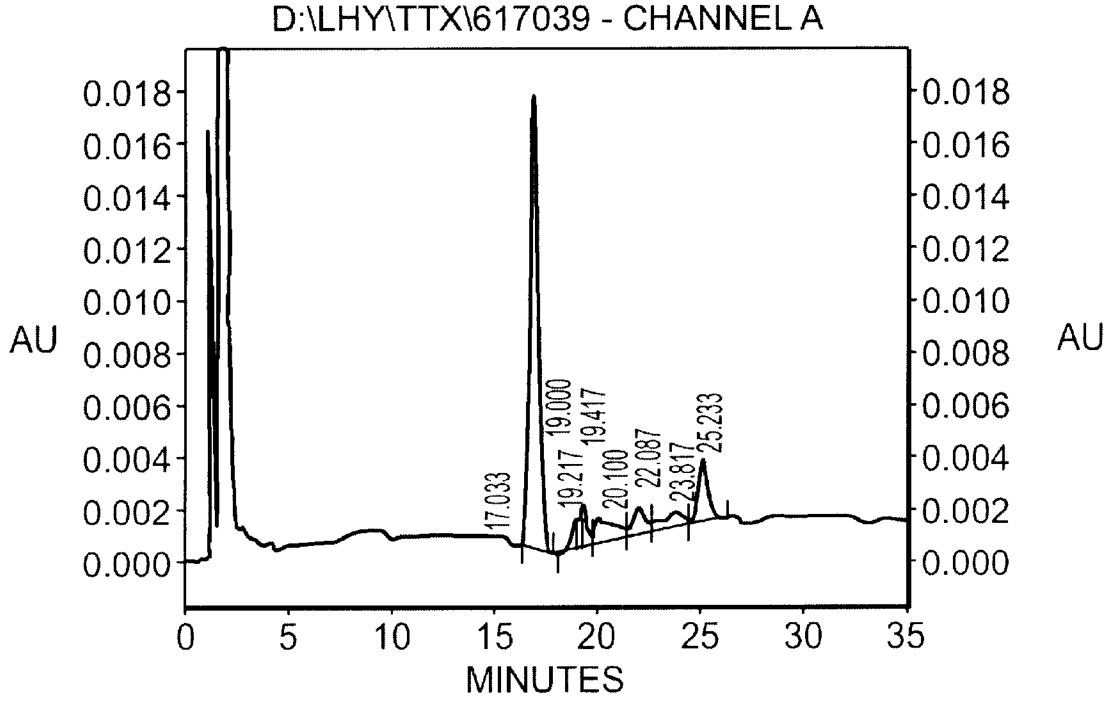
FIG. 17. Month 1 chromatogram of a sample of a TTX injection formulation (Batch 990120-1A) stored at 4–5° C.
Figure 18:
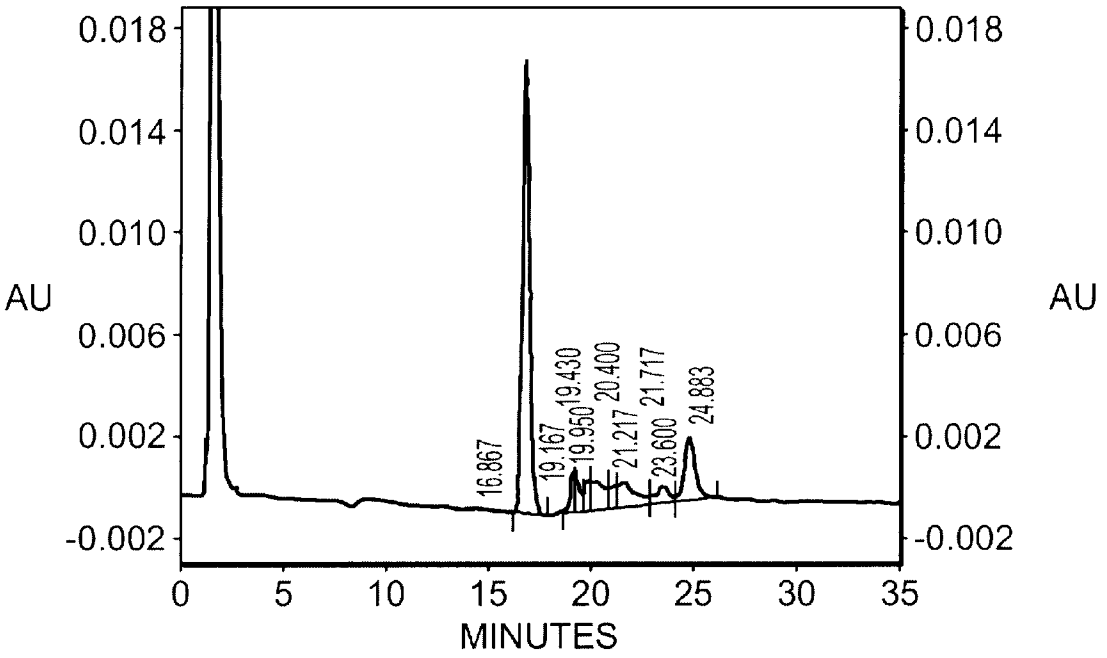
FIG. 18. Month 3 chromatogram of a sample of a TTX injection formulation (Batch 990120-1A) stored at 4–5° C.
Figure 19:
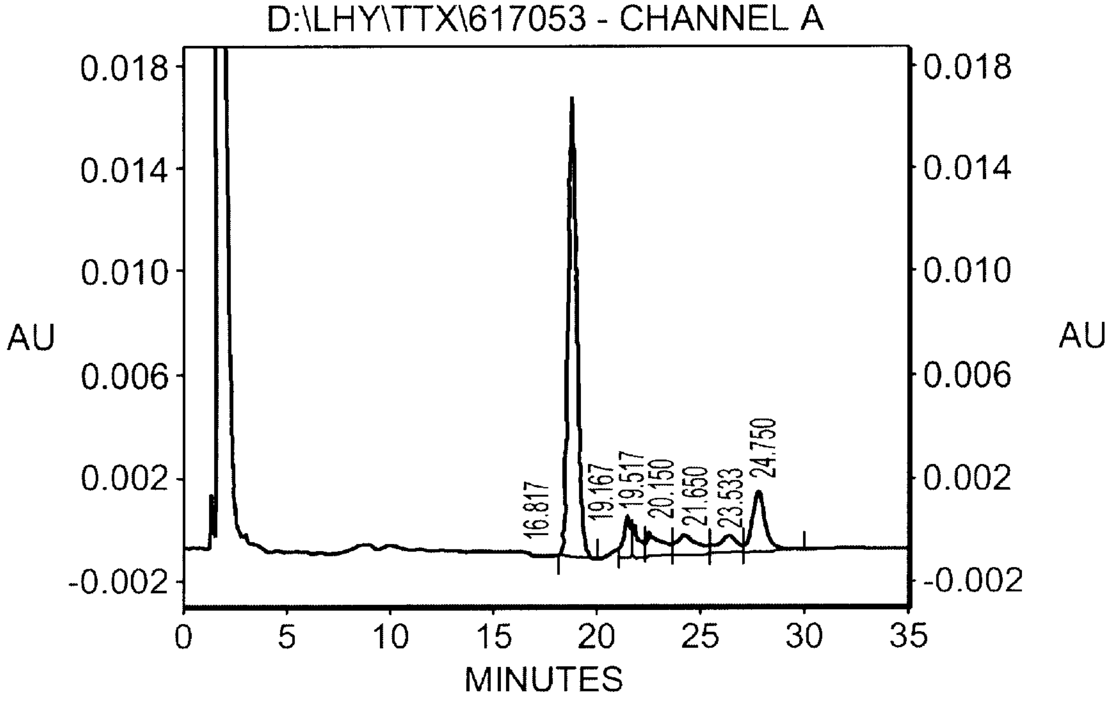
FIG. 19. Month 6 chromatogram of a sample of a TTX injection formulation (Batch 990120-1A) stored at 4–5° C.
Figure 20:
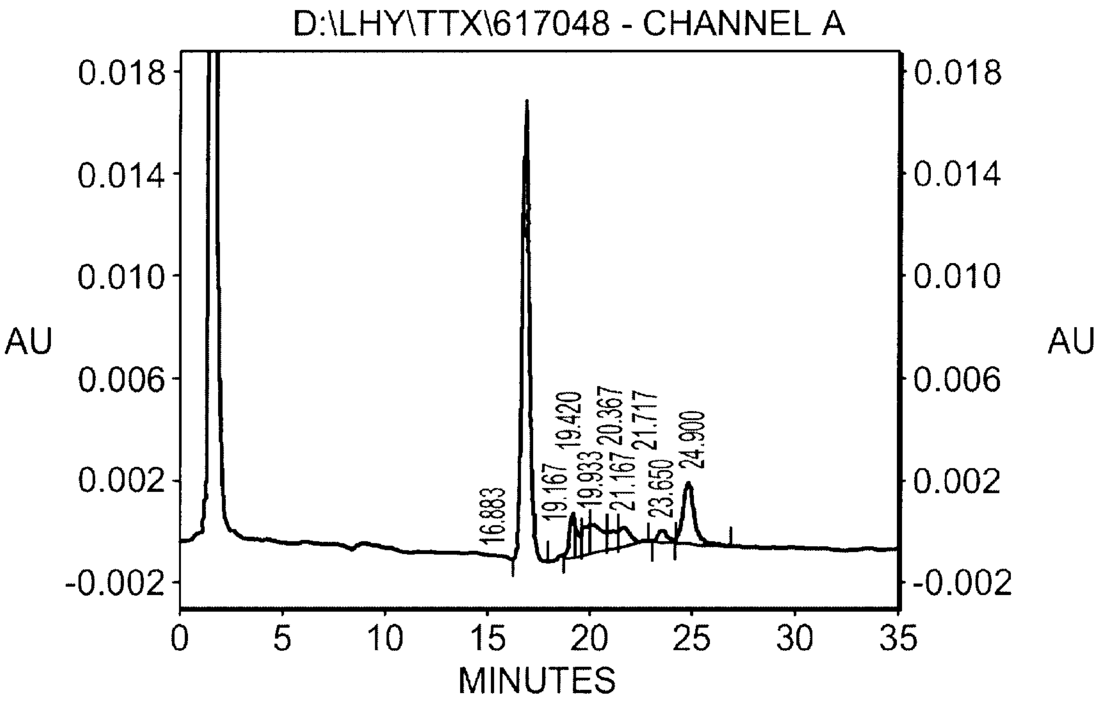
FIG. 20. Day 10 chromatogram of TTX injection samples (Batch 9901020-1A) stored at the humidity of 92.5%.
Figure 21:
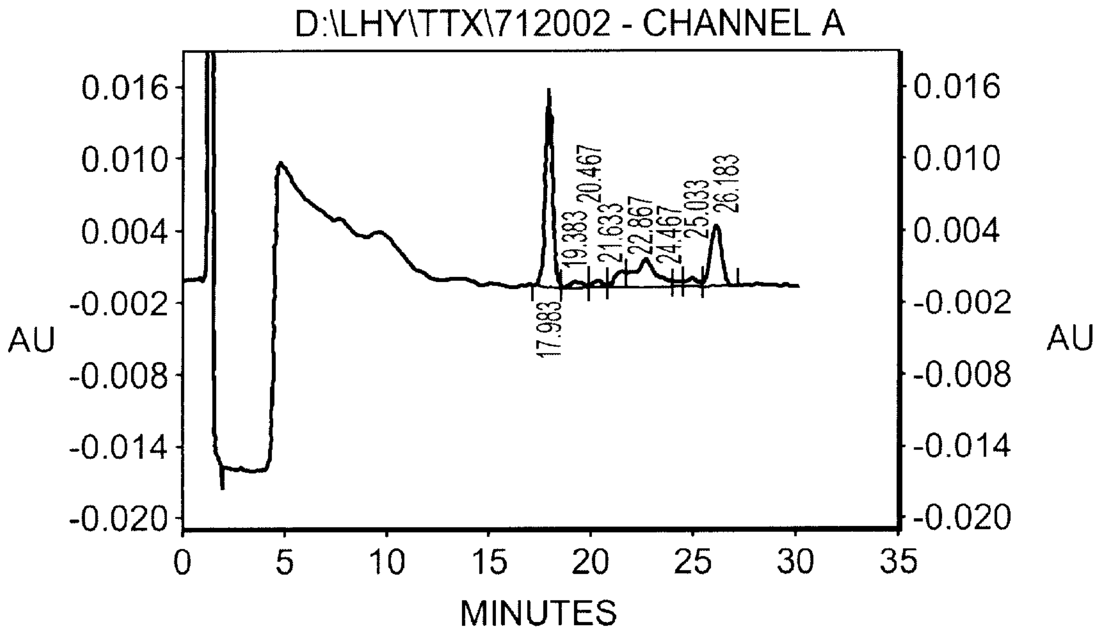
FIG. 21. Month 1 chromatogram of TTX injection samples (Batch 9901020-1A) in acceleration test at 40° C.
Figure 22:
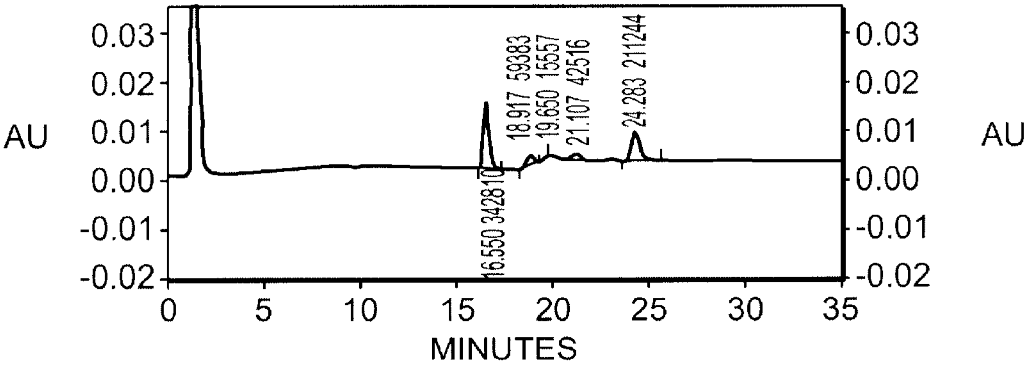
FIG. 22. Month 2 chromatogram of TTX injection samples (Batch 9901020-1A) in acceleration test at 40° C.
Figure 22:
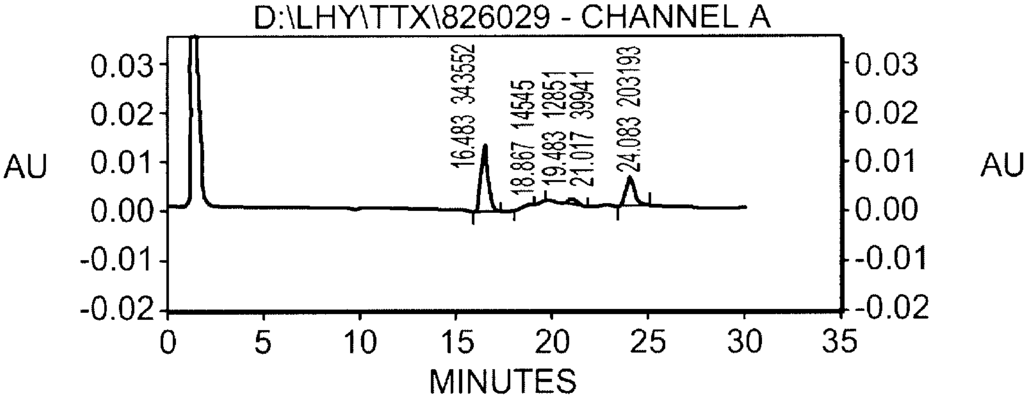
Figure 23:
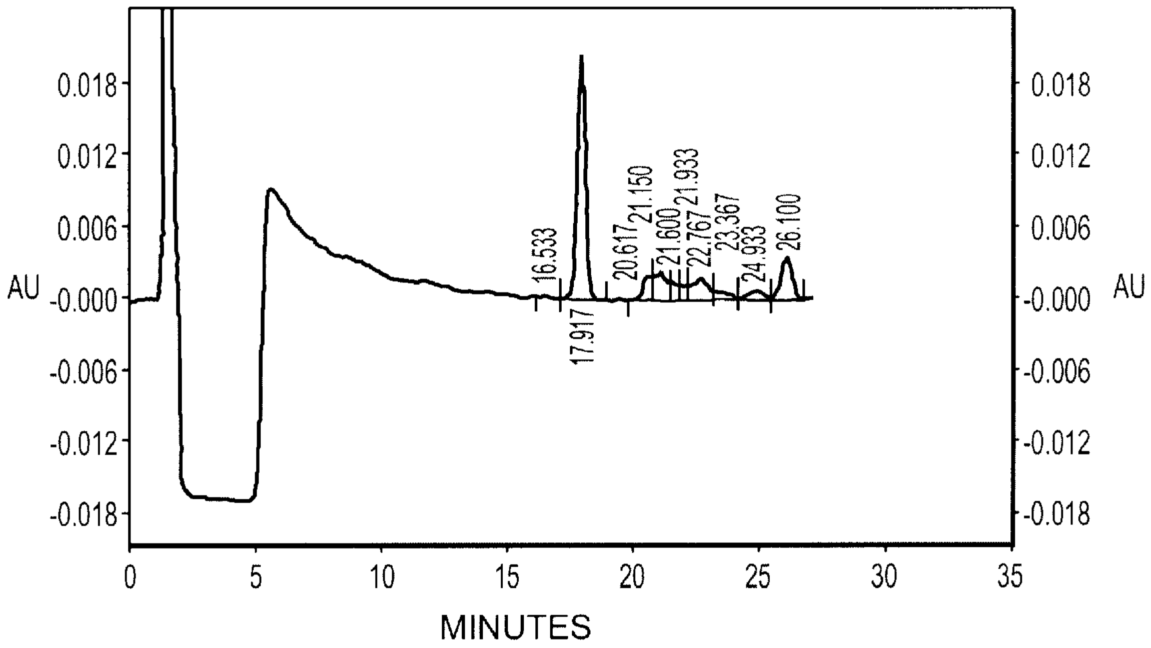
FIG. 23. Month 1 chromatogram of TTX injection samples (Batch 9901020-1A) in acceleration test at 4–5° C.
Figure 24:
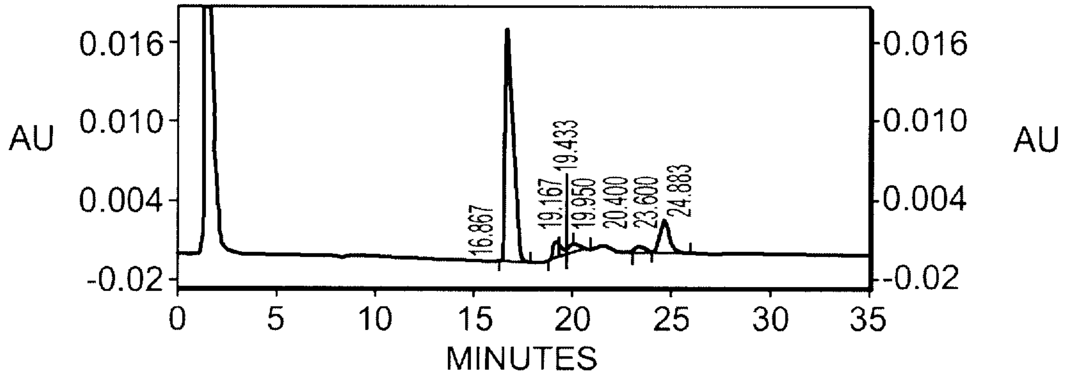
FIG. 24. Month 3 chromatogram of TTX injection samples (Batch 9901020-1A) in acceleration test at 4–5° C.
Figure 24:
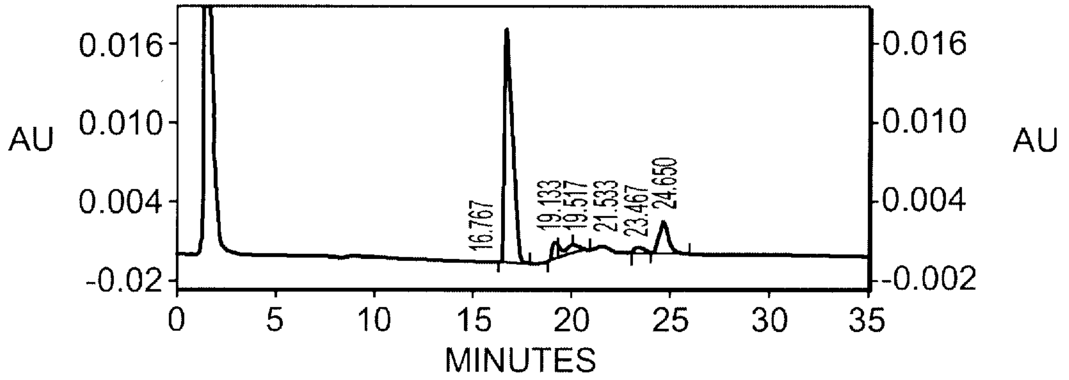
Figure 25:
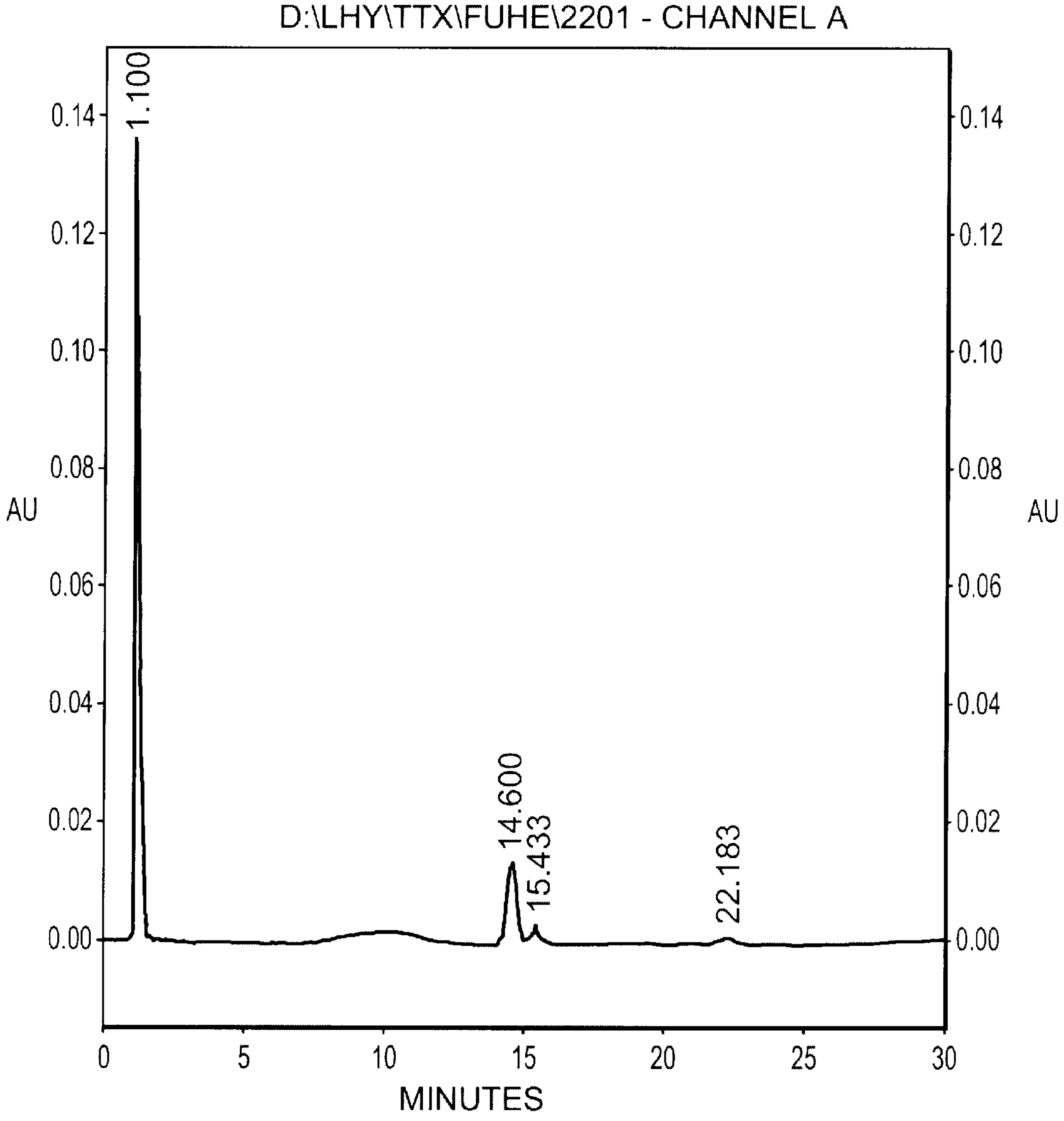
FIG. 25. Month 6 chromatogram of TTX injection samples (Batch 9901020-1A) in acceleration test at 4–5° C.

Take 100 μl of solutions A, C and D and inject into the HPLC system, respectively, and record their chromatograms (FIG. 5). Calculate the recovery. The examined recovery of tetrodotoxin was 101.8%.

| Solution | Tetro-dotoxin peak area | Average of Peak area | Average content of Tetrodotoxin (μg/100 ml) |
|---|---|---|---|
| C (0.2% acetic acid solution of the primary pharmaceutical) | 436671 | 436901.5 | 1.39659 |
| C (0.2% acetic acid solution of the primary pharmaceutical) | 437132 | | |
| D (Primary pharmaceutical + solution A) | 444093 | 444516 | 1.42256 |
| D (Primary pharmaceutical + solution A) | 444939 | | |
| A (Blank solvent) | 0 | | |

Recovery R (%)=1.42256/1.39659×100=101.85%≈101.8%

4.6 Sample Content Determination

Precisely take 100 μL of sample and inject into an HPLC column, record chromatogram (FIG. 4) and measure the peak area. The content is calculated based upon the standard calibration curve. The results of the samples of the three batches are as follows:

| Batch number | Content (%) |
|---|---|
| 990120-1A | 101.0 |
| 990121-2A | 108.5 |
| 990122-3A | 107.8 |

5. References

[1] Pharmacopoeia of P. R. China, Appendix, Vol. 2, 1995

[2] Compilation Of Guidelines For Pre-Clinical Studies Of New Drug (Western Medicine), 1993

[3] Huozhong Zhang and Yuling Wen, Chemistry of Animal Active Component. Tianjin Science and Technology Press, 1995

Example 3

Screening Best Proportions of Water and Propylene Glycol for TTX Formulation The stability of TTX in mixtures of various proportions of water and propylene glycol was determined. Mixtures of various proportions of water and propylene glycol were used to prepare TTX formulations, which were then heated in 100° C. water bath for 10 minutes, respectively.

Instrument and Reagents

- Waters 510 HPLC
- Electric heat water bath, Beijing Medical Equipment Factory
- TTX (purity 96.85%), Nanning Maple Leaf Pharmaceutical
- 1.2-propylene glycol, AR, Xinning Chemical Plant, Guangdong Experiment Design

| | | | | | Group |
|---|---|---|---|---|---|
| [Formula I] Control group | $R_0$ | TTX | 1.5 | mg | Group a |
| | | 0.5% acetic acid | 0.1 | mL | |
| | | (pH = 3.5) HAC-NaAC buffer | 5% | | |
| | $R_1$ | TTX | 1.5 | mg | Group A |
| | | 0.5% acetic acid | 0.1 | mL | |
| | | propylene glycol | 20 | mL | |
| | | water for injection, add to | 100 | mL | |
| | | (pH adjusted to 3.5 with 10% acetic acid | | | |
| | $R_2$ | TTX | 1.5 | mg | Group B |
| | | 0.5% acetic acid | 0.1 | mL | |
| | | propylene glycol | 40 | mL | |
| | | water for injection, add to | 100 | mL | |
| | | (pH adjusted to 3.5 with 10% acetic acid | | | |
| | $R_3$ | TTX | 1.5 | mg | Group C |
| | | 0.5% acetic acid | 0.1 | mL | |
| | | propylene glycol | 50 | mL | |

-continued

| | | | Group |
|---|---|---|---|
| | water for injection, add to | 100 mL | |
| | (pH adjusted to 3.5 with 10% acetic acid | | |
| $R_4$ | TTX | 1.5 mg | Group D |
| | 0.5% acetic acid | 0.1 mL | |
| | propylene glycol | 60 mL | |
| | water for injection, add to | 100 mL | |
| | (pH adjusted to 3.5 with 10% acetic acid | | |
| $R_5$ | TTX | 1.5 mg | Group E |
| | 0.5% acetic acid | 0.1 mL | |
| | propylene glycol | 70 mL | |
| | water for injection, add to | 100 mL | |
| | (pH adjusted to 3.5 with 10% acetic acid | | |
| $R_6$ | TTX | 1.5 mg | Group F |
| | 0.5% acetic acid | 0.1 mL | |
| | propylene glycol | 80 mL | |
| | water for injection, add to | 100 mL | |
| | (pH adjusted to 3.5 with 10% acetic acid | | |
| $R_7$ | TTX | 1.5 mg | Group B |
| | 0.5% acetic acid | 0.1 mL | |
| | propylene glycol | 100 mL | |
| | (pH adjusted to 3.5 with 10% acetic acid | | |

TTX formulations as described above were prepared and filled in 2 mL ampoules. Ampoules (6 each group) were then heated for 10 minutes in 100° C. water bath. Next, the content of TTX in samples from each group was examined and compared to that at Time 0, and the residual content of TTX in percentage was calculated for each group. Results are shown in Table 10.

TABLE 10

Residual TTX (%) in the mixed solvents of propylene glycol and water (heating time: 10 min. at 100° C.)

| Group (propylene glycol %) | a (control group) | A 20% | B 40% | C 50% | D 60% | E 70% | F 80% | G >95% |
|---|---|---|---|---|---|---|---|---|
| Residual TTX (%) | 83.50% | 84.70% | 86.60% | 88.75% | 89.50% | 88.30% | 88.70% | 88.20% |

Analysis and Conclusion

The stability of TTX, i.e. the residual content of TTX, increases generally with the proportion of propylene glycol. The residual content of TTX was kept around 88.5% when the proportion of propylene glycol is above 60% by volume. Addition of a proper amount of propylene glycol improves the stability of a TTX formulation.

The screening experiment above demonstrated that the stability of TTX formulation is improved in a mixed solvent of water and propylene glycol (pH adjusted to 3.5) compared to a carrier comprising acetic acid and a buffer. Therefore, TTX can be formulated with the mixed solvent of water and propylene glycol so as to improve its stability. The study also showed that the most preferable proportion of propylene glycol in the mixture with water is 60% for the stability of TTX formulation.

Example 4

Stability Study of Tetrodotoxin (TTX) Injection

The stability of tetrodotoxin (TTX) formulated for injection against light, heat and storage time under different storage conditions was investigated. The results indicated that light did not have noticeable effects on the TTX as formulated for injection, and no obvious changes were observed in the physical appearance and content. However, the product was sensitive to temperature; its content decreased with increasing temperature. It is recommended that TTX injection be stored at low temperature.

1. Purpose

To observe TTX injection stability against light, heat and storage time under various storage conditions by removing the packaging of a batch of tetrodotoxin injection formulation (Batch number 990120–1A).

2. Test Conditions 2.1 Light: Expose to fluorescent light (2000–4000 Lx) for 1, 3, 5 and 10 days.

2.2 High temperature: Expose to 40° C., 60° C. and 80° C. for 1, 3, 5 and 10 days.

2.3 Acceleration test: Expose to 40° C. and 75% RH for two months.

3. Test Items and Methods 3.1 Appearance: visual observation 3.2 Content determination: HPLC method (See Example 2 for details)

4. Test results

See Table 11, FIGS. 8 to 19.

5. Conclusion

The results showed that after exposing the one group of test samples to fluorescence (3000 Lx) their appearance and contents remain unchanged. When they were exposed to 40° C., 60° C. and 80° C., their appearance did not have significant changes, but their content decreased considerably. For the same storage time, the higher the temperature, the lower the content.

The results suggest that tetrodotoxin injection should be stored at low temperature (2° C.-8° C.).

TABLE 11

Stability study of Tetrodotoxin Injection (990120-1A)

| Test condition | Storage time | Appearance | Content (%) |
|---|---|---|---|
| Indoor temperature | 0 day | Colourless and clear liquid | 98.8 |
| light exposure | 1 day | Colourless and clear liquid | 93.7 |
| 3000LX | 3 days | Colourless and clear liquid | 95.4 |
| | 5 days | Colourless and clear liquid | 93.7 |
| | 10 days | Colourless and clear liquid | 93.8 |
| at 40° C. | 0 day | Colourless and clear liquid | 98.8 |
| | 1 day | Colourless and clear liquid | 90.8 |
| | 3 days | Colourless and clear liquid | 88.3 |
| | 5 days | Colourless and clear liquid | 86.4 |
| | 10 days | Colourless and clear liquid | 87.0 |
| at 60° C. | 0 day | Colourless and clear liquid | 98.8 |
| | 1 day | Colourless and clear liquid | 79.9 |
| | 3 days | Colourless and clear liquid | 72.0 |
| | 5 days | Colourless and clear liquid | 66.6 |
| | 10 days | Colourless and clear liquid | 64.9 |
| at 80° C. | 0 day | Colourless and clear liquid | 98.8 |
| | 1 day | Colourless and clear liquid | 55.2 |
| | 3 days | Colourless and clear liquid | 53.7 |
| | 5 days | Colourless and clear liquid | 45.2 |
| | 10 days | Colourless and clear liquid | 39.6 |
| Acceleration test | 0 day | Colourless and clear liquid | 98.8 |
| at 40° C. and | 1 month | Colourless and clear liquid | 75.65 |
| RH 75% | 2 months | Colourless and clear liquid | 71.49 |
| | 3 months | Colourless and clear liquid | n.d. |
| | 6 months | Colourless and clear liquid | n.d. |
| Storage at 4–5° C. | 0 day | Colourless and clear liquid | 98.8 |
| | 1 month | Colourless and clear liquid | 96.16 |
| | 3 months | Colourless and clear liquid | 95.43 |
| | 6 months | Colourless and clear liquid | 95.69 |

REFERENCES

[1] Pharmacopoeia of P. R. China, Vol. 2, 1995

[2] Compilation of Guidelines for Preclinical Research on New Drugs (Western Drugs), 1993.

[3] Standard Procedures of Drug Inspection of P. R. China

Various items of the scientific periodical and patent literature are cited herein. Each such item is hereby incorporated by reference in its entirety and for all purposes by such citation.

We claim:

1. A composition comprising:

at least one sodium channel blocking compound that specifically binds to a site on an SS1 region or an SS2 region of a sodium channel alpha subunit, and a pharmaceutically acceptable carrier comprising an aqueous solution of a weak organic acid and 50–80% propylene glycol and having a pH ranging from 3.0 to 5.0, wherein the sodium channel blocking compound is selected from the group consisting of tetrodotoxin, saxitoxin and analogs thereof.

2. The composition of claim 1, wherein the weak organic acid is acetic acid.

3. The composition of claim 1, wherein the analog of tetrodotoxin is anhydrotetrodotoxin, tetrodaminotoxin, methoxytetrodotoxin, ethoxytetrodotoxin, deoxytetrodotoxin or tetrodonic acid.

4. The composition of claim 1, which further comprises at least one auxiliary acidic solvent selected from the group consisting of dilute acetic acid, dilute hydrochloric acid and dilute citric acid.

5. The composition of claim 1, which further comprises at least one pH buffer selected from the group consisting of an acetate buffer, a citrate buffer, a phosphate buffer, and a borate buffer.

6. The composition of claim 1, which further comprises a vasoconstrictor, an antibiotic, or a steroidal or a non-steroidal anti-inflammatory drug.

7. The composition of claim 1, further comprising a preservative selected from the group consisting of benzalkonium chlorid, chlorobutanol, phenylmercuric acetate and phenyl mercuric nitrate.

8. The composition of claim 1, further comprising a tonicity adjustor selected from the group consisting of sodium chloride, mannitol and glycerine.

9. The composition of claim 1, further comprising a penetration enhancer selected from the group consisting of glycol, oleic acid, and an alkyl amine.

* * * * *